(12) United States Patent
Koeberle

(10) Patent No.: US 9,428,550 B2
(45) Date of Patent: Aug. 30, 2016

(54) PEPTIDES AND METHODS AND USES THEREOF FOR PREVENTING RETINAL DISORDERS

(71) Applicant: Governing Council of The University of Toronto, Toronto (CA)

(72) Inventor: Paulo Koeberle, Milton (CA)

(73) Assignee: Governing Council of the University of Toronto, Toronto (CA)

(*) Notice: Subject to any disclaimer, the term of this patent is extended or adjusted under 35 U.S.C. 154(b) by 0 days.

(21) Appl. No.: 14/373,073

(22) PCT Filed: Jan. 16, 2013

(86) PCT No.: PCT/CA2013/000034
§ 371 (c)(1),
(2) Date: Jul. 18, 2014

(87) PCT Pub. No.: WO2013/106909
PCT Pub. Date: Jul. 25, 2013

(65) Prior Publication Data
US 2014/0371161 A1    Dec. 18, 2014

Related U.S. Application Data

(60) Provisional application No. 61/587,970, filed on Jan. 18, 2012.

(51) Int. Cl.
| | | |
|---|---|---|
| *C07K 7/06* | (2006.01) | |
| *A61K 38/08* | (2006.01) | |
| *C07K 14/705* | (2006.01) | |
| *C12N 9/16* | (2006.01) | |
| *C07K 14/71* | (2006.01) | |
| *C12N 9/02* | (2006.01) | |
| *C12N 9/12* | (2006.01) | |
| *C07K 14/005* | (2006.01) | |

(52) U.S. Cl.
CPC . *C07K 7/06* (2013.01); *A61K 38/08* (2013.01); *C07K 14/005* (2013.01); *C07K 14/705* (2013.01); *C07K 14/71* (2013.01); *C12N 9/0075* (2013.01); *C12N 9/12* (2013.01); *C12N 9/16* (2013.01); *C07K 2319/00* (2013.01); *C07K 2319/10* (2013.01); *C12N 2740/16022* (2013.01)

(58) Field of Classification Search
CPC .... A61K 38/08; C07K 14/005; C07K 14/705; C07K 14/71; C07K 2319/00; C07K 2319/10; C07K 7/06; C12N 2740/16022; C12N 9/0075; C12N 9/12; C12N 9/16
See application file for complete search history.

(56) References Cited

U.S. PATENT DOCUMENTS

2008/0090770 A1* 4/2008 Belmares ........... A61K 38/1709
514/19.1

FOREIGN PATENT DOCUMENTS

| WO | 2000/28076 A1 | 5/2000 | |
|---|---|---|---|
| WO | 2004/092339 A2 | 10/2004 | |
| WO | 2006/007542 A1 | 1/2006 | |
| WO | 2007/018843 A2 | 2/2007 | |
| WO | 2007/019267 A1 | 2/2007 | |
| WO | WO 2011044701 A1 * | 4/2011 | .............. C12N 9/16 |

OTHER PUBLICATIONS

Francisca Vazquez, Phosphorylation of the PTEN Tail Regulates Protein Stability and Function, Molecular and Cellular Biology, Jul. 2000, p. 5010-5018.*
UniProtKB Accession Q3UUT8 (Q3UUT8_MOUSE), Gene name: PTEN from *Mus Musculus* (Mouse), First Entered Oct. 11, 2005.
UniProtKB Accession Q6PD97 ( Q6PD97_MOUSE), Gene name: kALRN from *Mus Musculus* (Mouse), First Entered Jul. 5, 2004.
Koeberle, P.D. et al., Kv1.1 and Kv1.3 channels contribute to the degeneration of retinal ganglion cells after optic nerve transection in vivo. Jan. 2010, Cell Death and Differentiation, vol. 17, pp. 134-144.
Koeberle, P.D. and Schlichter L.C., Targeting K(V) channels rescues retinal ganglion cells in vivo directly and by reducing inflammation. Sep./Oct. 2010, Channels, vol. 4, No. 5, pp. 337-346.
Koeberle, P.D. and Ball A.K., Nitric oxide synthase inhibition delays axonal degeneration and promotes the survival of axotomized retinal ganglion cells. Aug. 1999, Experimental Neurology, vol. 158, pp. 366-381.
Sun, Fang et al, Sustained Axon Regeneration Induced by Co-Deletion of PTEN and SOCS3, Nature, vol. 480, Dec. 15, 2011, pp. 372-376.
Park, Kevin Kyungsuk et al., Promoting Axon Regeneration in the Adult CNS by Modulation of the PTEN/mTOR Pathway, Science, vol. 322, Nov. 7, 2008, pp. 963-966.

* cited by examiner

*Primary Examiner* — James H Alstrum Acevedo
*Assistant Examiner* — Erinne Dabkowski
(74) *Attorney, Agent, or Firm* — Bereskin & Parr LLP; Melanie Szweras

(57) ABSTRACT

The present disclosure relates to methods and uses of C-terminal peptides for inhibiting neuronal cell death or dysfunction, such as retinal ganglion cell death or dysfunction, treating retinal degenerative disorders, stroke, CNS and PNS insults. The disclosure also relates to the C-terminal peptides, fusion proteins and compositions thereof.

12 Claims, 14 Drawing Sheets

Figure 3
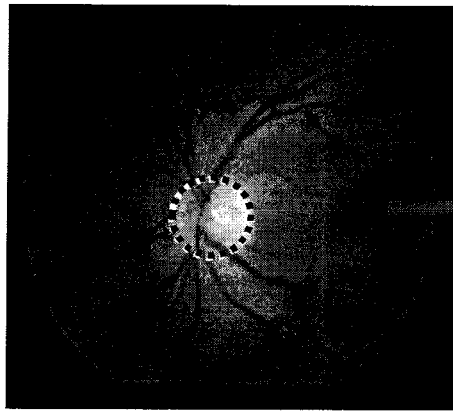
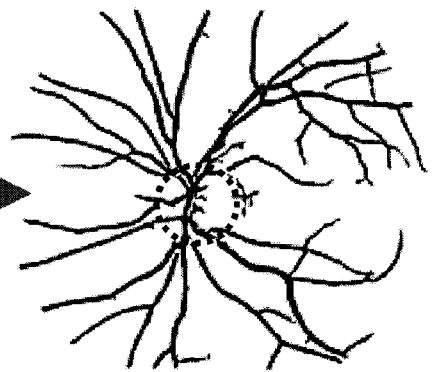
A
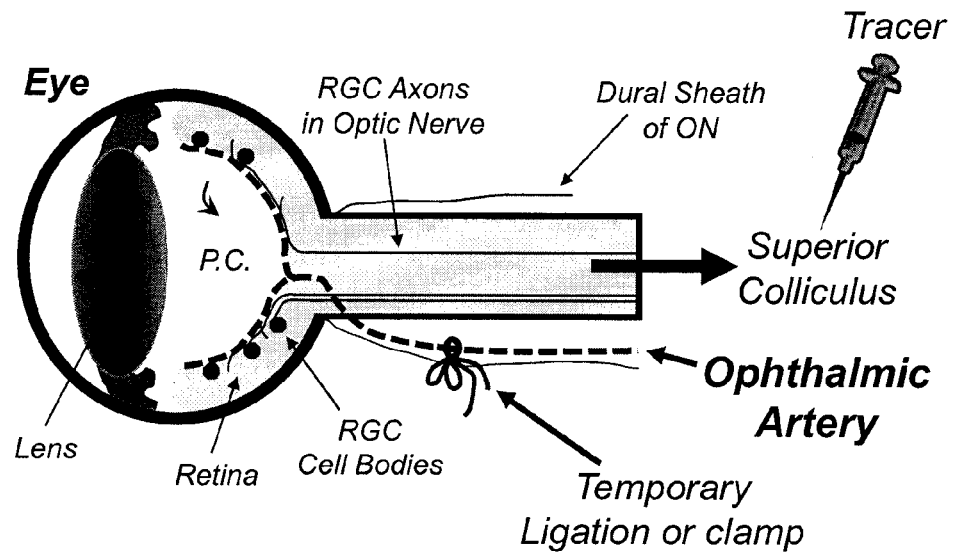
B

Figure 7
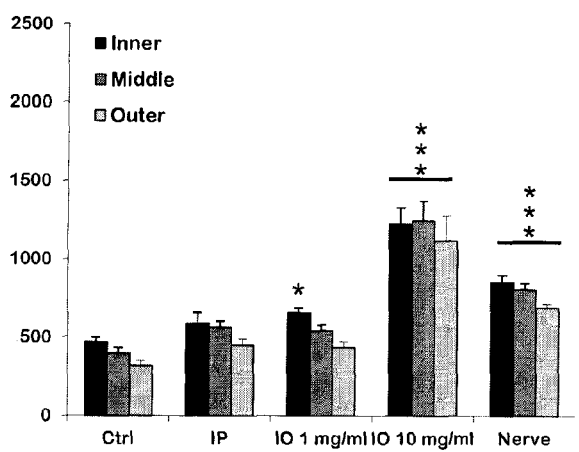
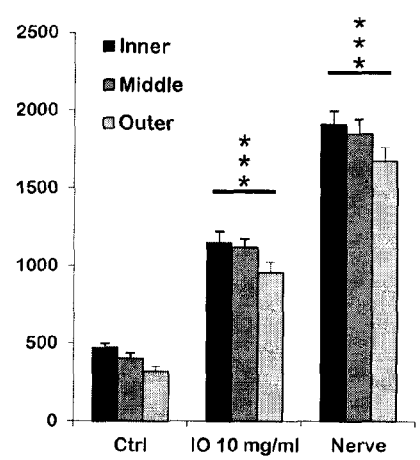
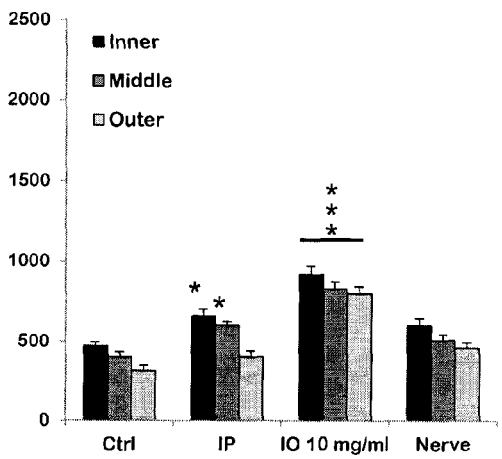
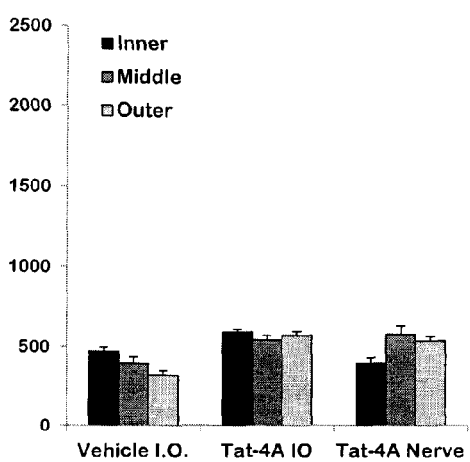

Figure 8
Peptides Protect Neurons After Ischemia
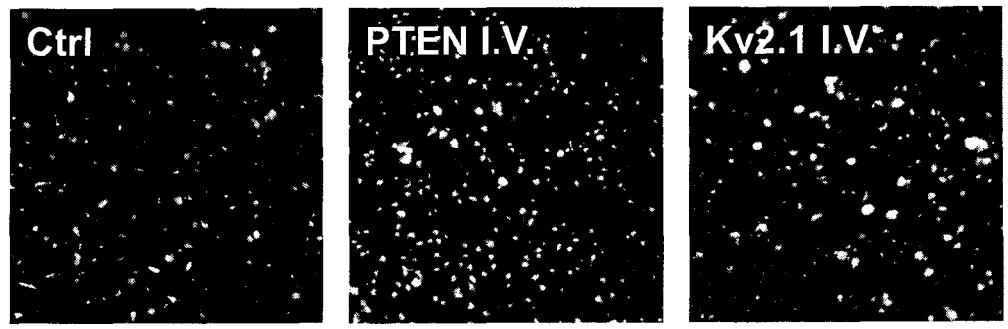
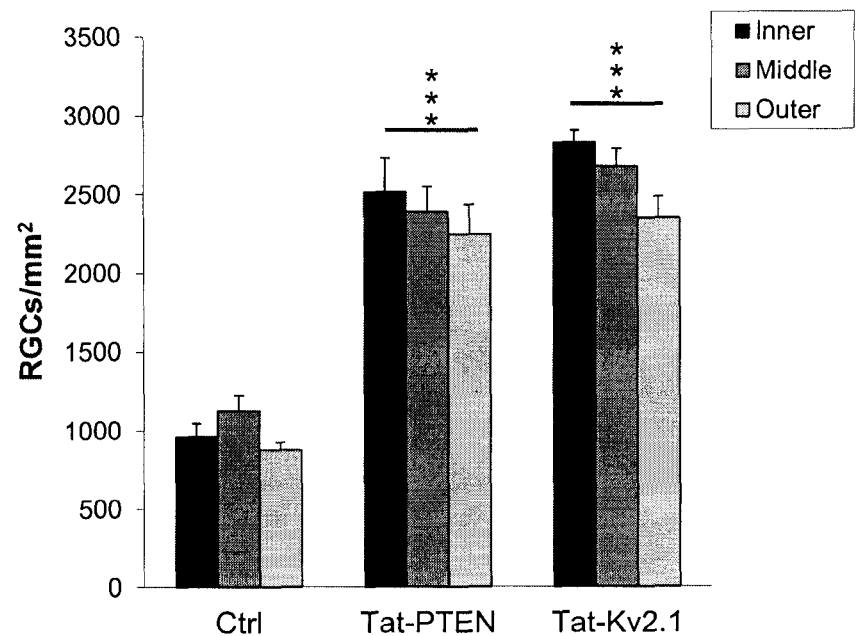

Figure 11  Optic Nerve Regeneration- TAT-PTEN

Figure 13
Protective effects of peptides after brain stroke (MCAO)
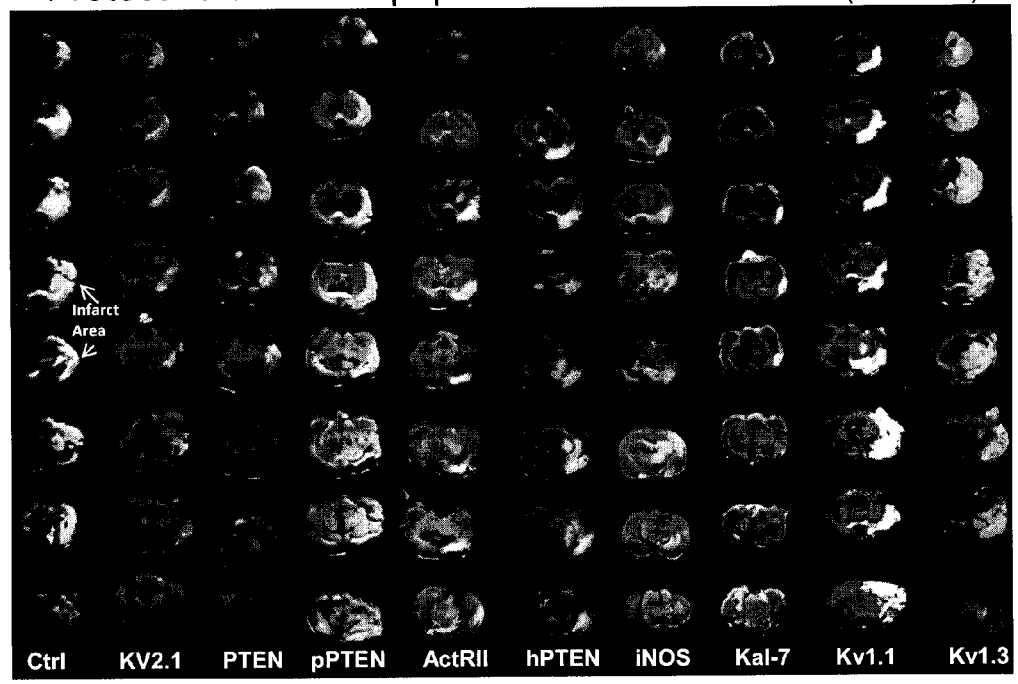
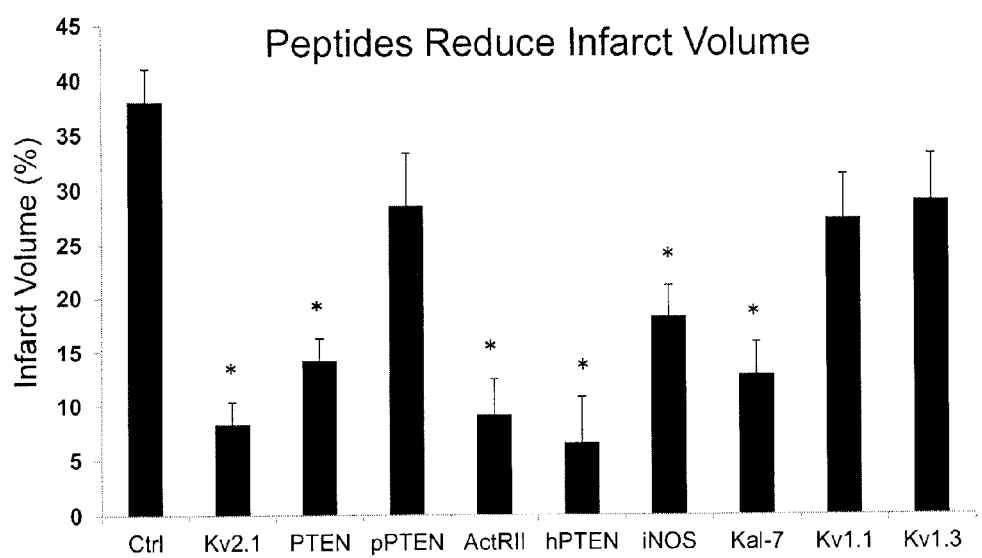

A
Effects of Peptides on Functional Neurological Deficits after MCAO

| Group | Baseline | 8Hrs | After MCAO 24 Hrs | 48 Hrs |
|---|---|---|---|---|
| Ctrl | 0(0-0) | 3.5(3–4) | 3 (2.5–3.5) | 3(2–3) |
| Kv2.1 | 0(0-0) | 3(3–4) | 3(2.75-3) | 2(1.5-2)* |
| PTEN | 0(0-0) | 3(2–4) | 3(2-3) | 2(2-2.5)* |
| pPTEN | 0(0-0) | 4(3–4) | 3(3-3) | 3(2-3) |
| ActRII | 0(0-0) | 3(2–3) | 2.5(2-3) | 2(1.5-2)* |
| hPTEN | 0(0-0) | 3(2.5–3.5) | 3(3-3) | 2(1.75-3)* |
| iNOS | 0(0-0) | 3(3–4) | 2.5(2-3.75) | 2(2-2)* |
| Kal-7 | 0(0-0) | 3(2–4) | 2(2-2)* | 2(1-2)* |
| Kv1.1 | 0(0-0) | 3.5(2.5–4) | 3(2-4) | 3(2-3) |
| Kv1.3 | 0(0-0) | 3(2.5–3.5) | 3(2.75-3) | 3(2-3) |

B

Effects of Peptides on Brain Edema

PEPTIDES AND METHODS AND USES THEREOF FOR PREVENTING RETINAL DISORDERS

CROSS REFERENCE TO RELATED APPLICATIONS

This application is a national phase entry of PCT/CA2013/000034 filed Jan. 16, 2013 (which designates the U.S.) which claims priority from U.S. provisional application No. 61/587,970 filed on Jan. 18, 2012 (now abandoned), all of which are incorporated herein by reference in their entirety.

INCORPORATION OF SEQUENCE LISTING

A computer readable form of the Sequence Listing "2223-P40203US01_SequenceListing.txt" (8,192 bytes), submitted via EFS-WEB and created on Jul. 17, 2014, is herein incorporated by reference.

FIELD

The disclosure relates to C-terminal peptides, fusion proteins and compositions, methods and uses thereof. In particular, the disclosure relates to methods of inhibiting neuronal cell death or dysfunction.

BACKGROUND

Glaucoma is the second leading cause of blindness, affecting at least 300,000 Canadians, and over 67,000,000 people worldwide. Retinal Ganglion cell (RGC) death is a major cause of visual impairment in optic neuropathies including glaucoma, AMD (Age Related Macular Degeneration), diabetic retinopathy, uveoretinitis and vitreo-retinopathy. Glaucoma is a disease in which the optic nerve and retinal ganglion cells are injured leading to peripheral vision loss and eventually blindness. Glaucoma is commonly characterized by an increase in intraocular pressure and is treated by ocular hypotensive drugs such as latanoprost. Despite the advent and therapeutic use of these drugs, vision loss as a result of RGC apoptosis and optic nerve atrophy continues, resulting in blindness.

Central nervous system (CNS) injury results in permanent functional loss due to the inability of adult CNS neurons to regenerate axons, and their susceptibility to programmed cell death (apoptosis). The unifying hallmark of visual diseases such as glaucoma and optic neuropathies is the death of Retinal Ganglion Cells (RGCs) of the eye. RGCs are CNS neurons that transmit visual information from the retina to the brain via the optic nerve. The optic nerve can be accessed within the orbit of the eye and completely cut (axotomized), transecting the axons of the entire RGC population. Optic nerve transection (FIG. 1) is a reproducible model of apoptotic neuronal cell death in the adult CNS (Bahr 2000; Koeberle and Bahr 2004; Magharious, D'Onofrio et al. 2011; Magharious, D'Onofrio et al. 2011). The optic nerve transection model is particularly attractive because the vitreous chamber of the eye acts as a capsule for drug delivery to the retina, permitting experimental manipulations. The diffusion of chemicals through the posterior chamber fluid ensures that they act upon the entire RGC population. Moreover, RGCs can be selectively transfected by applying short interfering RNAs (siRNAs), plasmids, or viral vectors to the cut end of the optic nerve (Garcia Valenzuela and Sharma 1998; Kugler, Klocker et al. 1999; Lingor, Koeberle et al. 2005; Koeberle and Schlichter 2010; Koeberle, Wang et al. 2010). This permits selective therapeutic targeting of RGCs without confounding effects on bystander neurons or surrounding glia. An additional benefit is the accuracy with which cell survival can be quantified after injury. The retina is a flat tissue and RGCs are located in the innermost layer, the ganglion cell layer. The survival of injured RGCs can be tracked by applying a fluorescent tracer (3% Fluorogold) to the cut end of the optic nerve at the time of axotomy, or by injecting the tracer into the superior colliculus (RGC target) one week prior to axotomy. Tracers applied by these methods are retrogradely transported back to the RGC cell bodies, labeling all of the RGCs in the retina. RGC survival is then quantified by fixing the eye, removing the retina, and flat-mounting the tissue (FIG. 2). In this preparation, the ganglion cell layer, which is a monolayer (one cell in thickness), is imaged in order to calculate the number of cells per unit area (cells/mm$^2$) (FIG. 2). Optic nerve transection causes the apoptotic death of 90% of injured RGCs within 14 days postaxotomy (Villegas-Perez, Vidal-Sanz et al. 1988; Villegas-Perez, Vidal-Sanz et al. 1993; Berkelaar, Clarke et al. 1994; Peinado-Ramon, Salvador et al. 1996). RGC apoptosis has a characteristic time-course whereby cell death is delayed 3-4 days postaxotomy, after which the cells rapidly degenerate (FIG. 2). This provides a time window for experimental manipulations directed at developing therapeutics for CNS insults.

Stroke (ischemia) of the CNS can be studied via ophthalmic artery ligation. Ligature of the ophthalmic vessels (FIG. 3), without damaging the optic nerve, causes 50% RGC death within 14 days (Lafuente, Villegas-Perez et al. 2002). RGCs die by the process of apoptosis following axotomy, ischemia, and during the course of glaucoma (Berkelaar, Clarke et al. 1994; Quigley, Nickells et al. 1995; Bahr 2000; Lafuente, Villegas-Perez et al. 2002; Koeberle and Bahr 2004), hence these animal models provide a testing ground for therapeutics that can be directly applied in a clinical situation in order to prevent RGC death. Furthermore, the therapeutics developed via studies in these models are applicable to the treatment of insults in other regions of the CNS such as the brain or spinal cord, that include traumatic CNS injury, stroke, concussion, neurodegenerative diseases, and brain damage caused by tumours or surgical procedures.

SUMMARY

The present inventor has demonstrated that several peptides that target protein-protein interactions dependent on C-terminal binding interactions have neuroprotective effects on axotomized RGCs. These peptides show a several-fold improvement in RGC survival in comparison to other therapeutics, including neurotrophic factors and clinically relevant small molecules (Sievers, Hausmann et al. 1987; Mey and Thanos 1993; Peinado-Ramon, Salvador et al. 1996; Klocker, Braunling et al. 1997; Di Polo, Aigner et al. 1998; Garcia Valenzuela and Sharma 1998; Kermer, Klocker et al. 1998; Koeberle and Ball 1998; Chaudhary, Ahmed et al. 1999; Kermer, Klocker et al. 1999; Koeberle and Ball 1999; Kermer, Ankerhold et al. 2000; Leon, Yin et al. 2000; Yip and So 2000; Koeberle and Ball 2002; Lafuente, Villegas-Perez et al. 2002; Nakazawa, Tamai et al. 2002; Koeberle, Gauldie et al. 2004; Wu, Lai et al. 2004; Marrazzo, Caraci et al. 2005; Cantarella, Bucolo et al. 2007; Lingor, Tonges et al. 2008; Koeberle and Schlichter 2010; Koeberle, Tura et al. 2010; Magharious, D'Onofrio et al. 2011; Monnier, D'Onofrio et al. 2011). Use of combinations of the peptides permits simultaneous blocking of redundant cell death pathways providing increased efficacy.

Accordingly, in one aspect, the present disclosure provides a method of inhibiting neuronal cell death or dysfunction comprising administering at least one C-terminal peptide to an animal or cell in need thereof, wherein the C-terminal peptide comprises an amino acid sequence as shown in SEQ ID NOs:1-6, 8 or 9 or a variant or analog thereof.

Also included is use of at least one C-terminal peptide for inhibiting neuronal cell death or dysfunction in an animal or cell in need thereof, wherein the C-terminal peptide comprises an amino acid sequence as shown in SEQ ID NOs:1-6, 8 or 9 or a variant or analog thereof. Further provided is use of at least one C-terminal peptide in the preparation of a medicament for inhibiting neuronal cell death or dysfunction in an animal or cell in need thereof, wherein the C-terminal peptide comprises an amino acid sequence as shown in SEQ ID NOs:1-6, 8 or 9 or a variant or analog thereof. Even further provided is at least one C-terminal peptide for use in inhibiting neuronal cell death or dysfunction in an animal or cell in need thereof, wherein the C-terminal peptide comprises an amino acid sequence as shown in SEQ ID NOs:1-6, 8 or 9 or a variant or analog thereof. In one embodiment, the at least one C-terminal peptide consists of the amino acid sequence as shown in SEQ ID NOs:1-6, 8 or 9.

In one embodiment, the method or uses for inhibiting neuronal cell death or dysfunction comprise administering at least one C-terminal peptide to an animal or cell in need thereof, wherein the C-terminal peptide comprises an amino acid sequence as shown in SEQ ID NOs:1, 2, 5, 6, 8 or 9 or a variant or analog thereof.

In one embodiment, the method or uses for inhibiting neuronal cell death or dysfunction comprise administering at least one C-terminal peptide to an animal or cell in need thereof, wherein the C-terminal peptide comprises an amino acid sequence as shown in SEQ ID NOs:1 or 9 or a variant or analog thereof.

In another embodiment, the method or uses for inhibiting neuronal cell death or dysfunction comprise administering at least one C-terminal peptide to an animal or cell in need thereof, wherein the C-terminal peptide comprises an amino acid sequence as shown in SEQ ID NO:2 or a variant or analog thereof.

In one embodiment, the present disclosure provides a method of inhibiting retinal ganglion cell death or dysfunction comprising administering at least one C-terminal peptide to an animal or cell in need thereof, wherein the C-terminal peptide comprises an amino acid sequence as shown in SEQ ID NOs:1-6, 8 or 9 or a variant or analog thereof. Also included is use of at least one C-terminal peptide for inhibiting retinal ganglion cell death or dysfunction in an animal or cell in need thereof, wherein the C-terminal peptide comprises an amino acid sequence as shown in SEQ ID NOs:1-6, 8 or 9 or a variant or analog thereof. Further provided is use of at least one C-terminal peptide in the preparation of a medicament for inhibiting retinal ganglion cell death or dysfunction in an animal or cell in need thereof, wherein the C-terminal peptide comprises an amino acid sequence as shown in SEQ ID NOs:1-6, 8 or 9 or a variant or analog thereof. Even further provided is at least one C-terminal peptide for use in inhibiting retinal ganglion cell death or dysfunction in an animal or cell in need thereof, wherein the C-terminal peptide comprises an amino acid sequence as shown in SEQ ID NOs:1-6, 8 or 9 or a variant or analog thereof. In one embodiment, at least two, three, four, five or six of the C-terminal peptides are administered or used. In one embodiment, the C-terminal peptide comprises the amino acid sequence as shown in SEQ ID NOs: 1, 2, 5, 6, 8 or 9. In another embodiment, the C-terminal peptide comprises the amino acid sequence as shown in SEQ ID NOs: 1 or 9. In another embodiment, the C-terminal peptide comprises the amino acid sequence as shown in SEQ ID NO: 2. In one embodiment, the at least one C-terminal peptide consists of the amino acid sequence as shown in SEQ ID NOs:1-6, 8 or 9.

In another embodiment, the C-terminal peptides as shown in SEQ ID NO:1 and 2 or a variant or analog thereof are administered or used. In another embodiment, the C-terminal peptides as shown in SEQ ID NO:9 and 2 or a variant or analog thereof are administered or used.

In another embodiment, the at least one C-terminal peptide is modified for cell permeability, stability or bioavailability. In one embodiment, a protein transduction domain is conjugated to the at least one C-terminal peptide. In an embodiment, the protein transduction domain is a TAT protein transduction domain, such as the domain shown in SEQ ID NO: 7 or a variant or analog thereof. In another embodiment, the protein transduction domain is an arginine 9-mer (RRRRRRRRR: also referred to as "R9"), such as the domain shown in SEQ ID NO:11 or a variant or analog thereof. In yet another embodiment, the protein transduction domain is a lysine 9-mer (KKKKKKKKK: also referred to as "K9"), such as the domain shown in SEQ ID NO:10 or a variant or analog thereof.

In yet another embodiment, the animal has or is at risk of having a retinal degenerative disorder. In an embodiment, the retinal degenerative disorder is disorder is glaucoma, age related macular degeneration, diabetic retinopathy, uveoretinitis, vitreo-retinopathy, photoreceptor cell dystrophy or degeneration, retinitis pigmentosa, retinal ischemia, retinal detachment, optic neuropathy or optic atrophy. In one embodiment, the retinal degenerative disorder is glaucoma.

In another embodiment, the C-terminal peptide comprises an amino acid sequence as shown in SEQ ID NOs:1, 2, 5, 6, 8 or 9 or a variant or analog thereof and the animal had a stroke, is having a stroke, or is at risk of having a stroke (ischemic or hemorrhagic).

In yet another embodiment, the animal is in need of treatment of insults in other regions of the CNS such as the brain or spinal cord, including, without limitation, traumatic CNS injury, stroke, concussion, neurodegenerative diseases, and brain damage caused by tumours or surgical procedures.

In a further embodiment, the animal is in need of treatment for an insult to the PNS such as diabetic neuropathy, amyloid neuropathy, brachial plexus neuropathy, neuralgia, neuritis, nerve compression syndrome, polyneuropathy, peripheral nervous system neoplasm and peripheral pain syndrome.

The at least one C-terminal peptide may be administered or used in any manner, including, without limitation, intravenously, intraocularly, via optic nerve injection, topically, intraperitoneally, by surgically implantation, intrathecally, or via direct injection into the CNS (including brain or spinal cord).

In one embodiment, the at least one C-terminal peptide is administered topically or is for topical use. In an embodiment, the at least one C-terminal peptide comprises an amino acid sequence as shown in SEQ ID NOs:1, 2, 3, 5, 6, 8 or 9 or a variant or analog thereof and the topical treatment is applied to the eye or is for use in the eye, for example in the form of eye drops, a topical ointment or a liquid.

Also provided herein are the C-terminal peptides, fusion proteins and compositions thereof.

Other features and advantages of the present disclosure will become apparent from the following detailed description. It should be understood, however, that the detailed description and the specific examples while indicating embodiments of the disclosure are given by way of illustration only, since various changes and modifications within the spirit and scope of the disclosure will become apparent to those skilled in the art from this detailed description.

BRIEF DESCRIPTION OF THE DRAWINGS

The disclosure will now be described in relation to the drawings in which:

FIG. 3a shows retinal vasculature. When the ophthalmic artery enters the retina at the optic disc, its branches fan out over the inner retina like the spokes of a wheel. A computer model of the in vivo image on the left is shown to the right. The arteries would show this layout in a flatmounted rat retina. These arteries supply blood to the inner retina, including the ganglion cell layer that contains all the RGCs. The optic disc has been labeled with a dotted circle (see world wide web at vcipl.okstate.edu/localentropy.htm).

FIG. 3b shows ophthalmic artery ligation. Opthalmic artery ligation is a model of ischemic CNS injury where the ophthalmic artery that supplies blood to the inner retina is temporarily ligated, without damaging the optic nerve. The ophthalmic artery travels through the meningeal sheath that surrounds the optic nerve, and enters the eye at the optic disc, where RGC axons exit. The radial branches of the ophthalmic artery branch out over the inner retina like the spokes of a wheel (FIG. 3a). RGCs are retrogradely pre-labeled by injecting a fluorescent tracer into their target, the superior colliculus, one week prior to injury. The tracer is retrogradely transported, labeling the cell bodies in the retina. The effects of different treatments on RGC survival were quantified by injecting peptides intravenously.

FIG. 7 shows quantification of RGC survival after axotomy. RGC densities expressed as the mean number of cells/mm$^2$ (±SEM) on the vertical axis. RGC densities were quantified at 3 different distances (eccentricities) from the optic disc in the center of the retina; inner, mid-periphery, outer. RGC density in the normal un-injured eye is ~2500 cells/mm$^2$ (Top of Vertical Axis). RGC survival was quantified at 14 days postaxotomy, following TAT-PTEN (A), TAT-Kv2.1 (B), or TAT-iNOS (C) treatment. *=$p<0.05$ relative to control, ***=$p<0.001$ relative to control. Additional controls (D) were intraocular injection of TAT-polyalanine, and nerve injection of TAT-polyalanine. IO=intraocular injection, Nerve=nerve injection.

FIG. 8 shows quantification of RGC survival after stroke (ophthalmic artery ligation). (TOP) Epifluorescence micrographs of Fluorogold retrogradely labeled RGCs in Control (Ctrl) animals, or animals that received TAT-PTEN or TAT-Kv2.1 via intravenous injection. Animals had the ophthalmic vessels ligated for 45 minutes, and received two I.V. peptide injections (24 hours and 8 days after injury) of 0.5 mg of each peptide. (BOTTOM) RGC densities expressed as the mean number of cells/mm$^2$ (±SEM) on the vertical axis. RGC densities were quantified at 3 different distances (eccentricities) from the optic disc in the center of the retina; inner, mid-periphery, outer. RGC survival was quantified at 14 days after stroke. ***=$p<0.001$ relative to control.

FIG. 13 shows the quantification of the therapeutic effects of C-terminal peptides after stroke of the middle cerebral artery (MCA), in adult rats. Arginine 9-mer-conjugated C-terminal peptides were delivered via intravenous injections (tail-vein) after middle cerebral artery occlusion (MCAO), and quantified brain infarct volume at 48 hours after MCAO. The top black panel shows 10 vertical columns, each containing 8 images, with the corresponding treatment labeled at the bottom in white lettering. Each of the 8 brain images in a column is the coronal face of a 2 mm thick brain section, in sequential order from anterior (rostral) to posterior (caudal) from top to bottom respectively. These brain sections were stained using the TTC procedure: 2,3,5-triphenyltetrazolium chloride solution (TTC) is metabolized by live cells, turning the viable regions of the brain a reddish-brown color (grey in these images); whereas dead regions of brain tissue remain white. The mean volume of infarcted brain (±SEM) tissue at 48 hours after stroke is quantified in the bottom panel of FIG. 13. *=$p<0.05$ relative to control (Ctrl).

DETAILED DESCRIPTION

Figure 1:
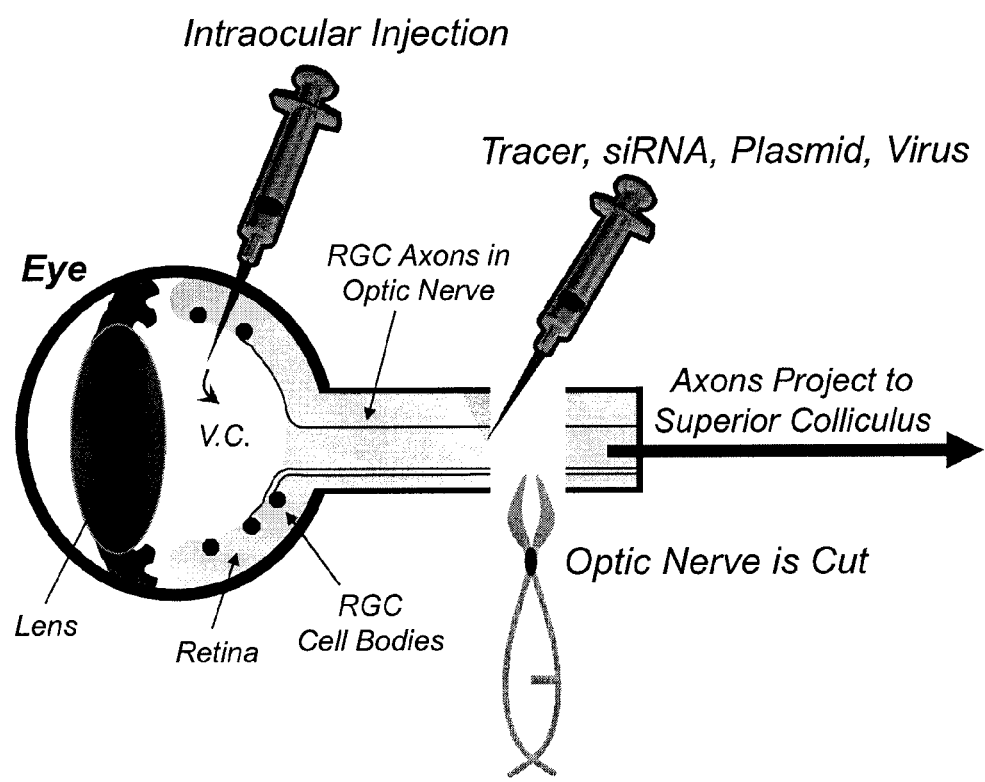
FIG. 1 shows optic nerve transection. Optic nerve transection is a model of traumatic CNS injury where the axons of the retinal ganglion cells (RGCs) are all transected just behind the eye. RGC axons exit the back of the eye at the optic disc, where they bundle to form the optic nerve. The optic nerve carries visual information from the retina to the Superior Colliculus in the diencephalon of the brain. RGCs are retrogradely labeled by applying a fluorescent tracer to the cut ends of their axons. The tracer is retrogradely transported, labeling the cell bodies in the retina within 24 hours. The effects of different treatments on RGC survival can be assessed by injecting substances into the vitreous chamber of the eye. The Vitreous Chamber (V.C.) acts like self-contained capsule for drug delivery to the retina. Similar to tracers, siRNAs, plasmids, or viral vectors can be applied to the cut end of the optic nerve in order to selectively transfect RGCs.
Figure 2:
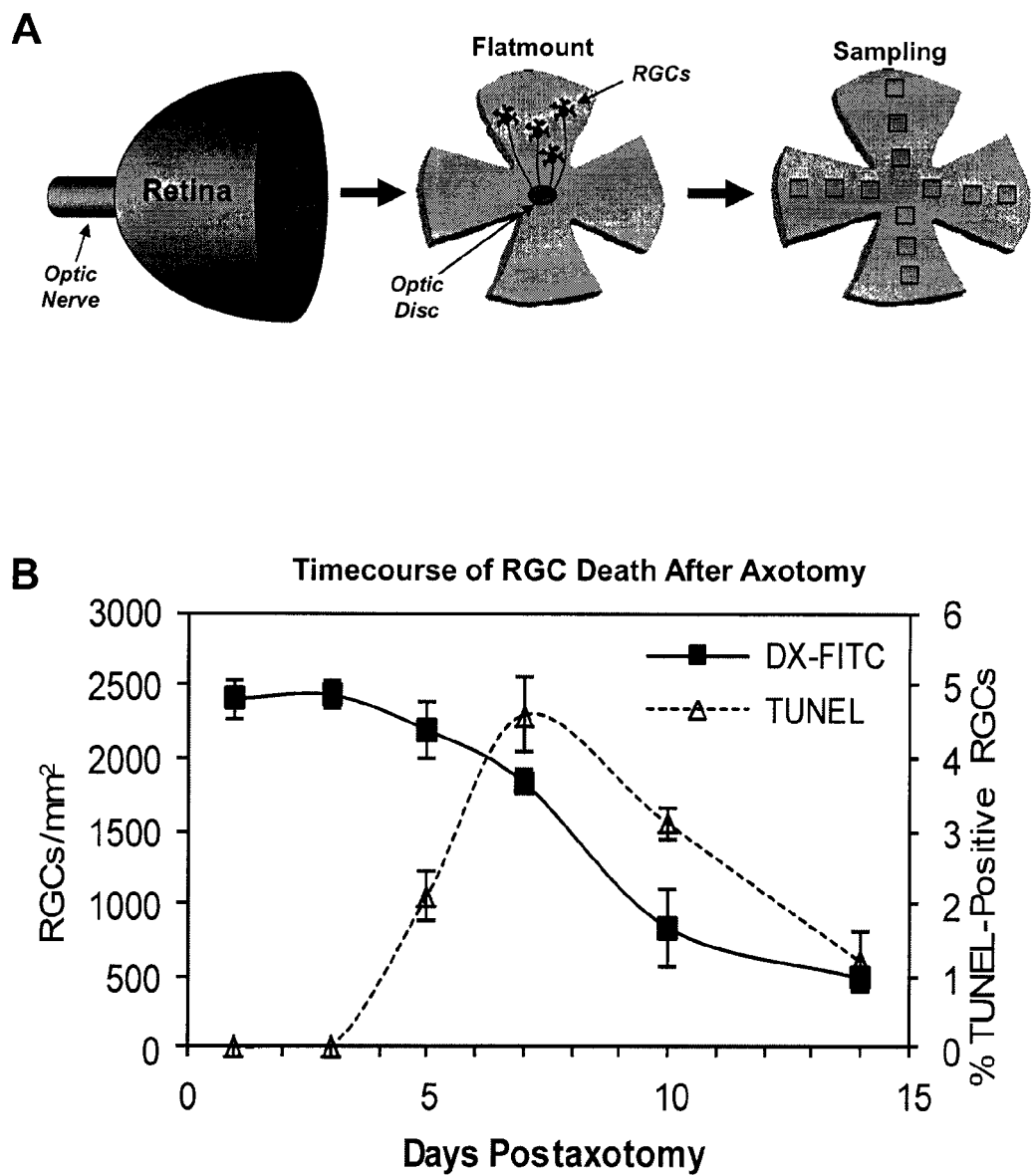
FIG. 2a shows a schematic of the fixed retina. The fixed retina is cup-shaped. By making 4 radial cuts, the retina can be flatmounted, and RGC densities sampled in different regions of the retina. Because the ganglion cell layer is a monolayer, one cell thick, the density of RGCs can easily be calculated as the number of cells per unit area (RGCs/mm$^2$). Samples are taken at different eccentricities of each quadrant (inner, middle, outer). RGC axons converge towards the optic disc where they pass through the retina, exit the eye and form the optic nerve.
FIG. 2b shows a time course of retinal ganglion cell death after axotomy. Apoptotic RGC degeneration after axotomy has a characteristic timecourse. There is a 3-4 day delay before significant apoptosis begins, after which RGCs rapidly degenerate. This leads to the death of 90% of cells by 14 days postaxotomy (solid line/circles). TUNEL staining (hatched line/open squares), which detects fragmented DNA that is a hallmark of apoptosis, peaks at 7 days postaxotomy, when the rate of RGC death is the greatest.
Figure 4:
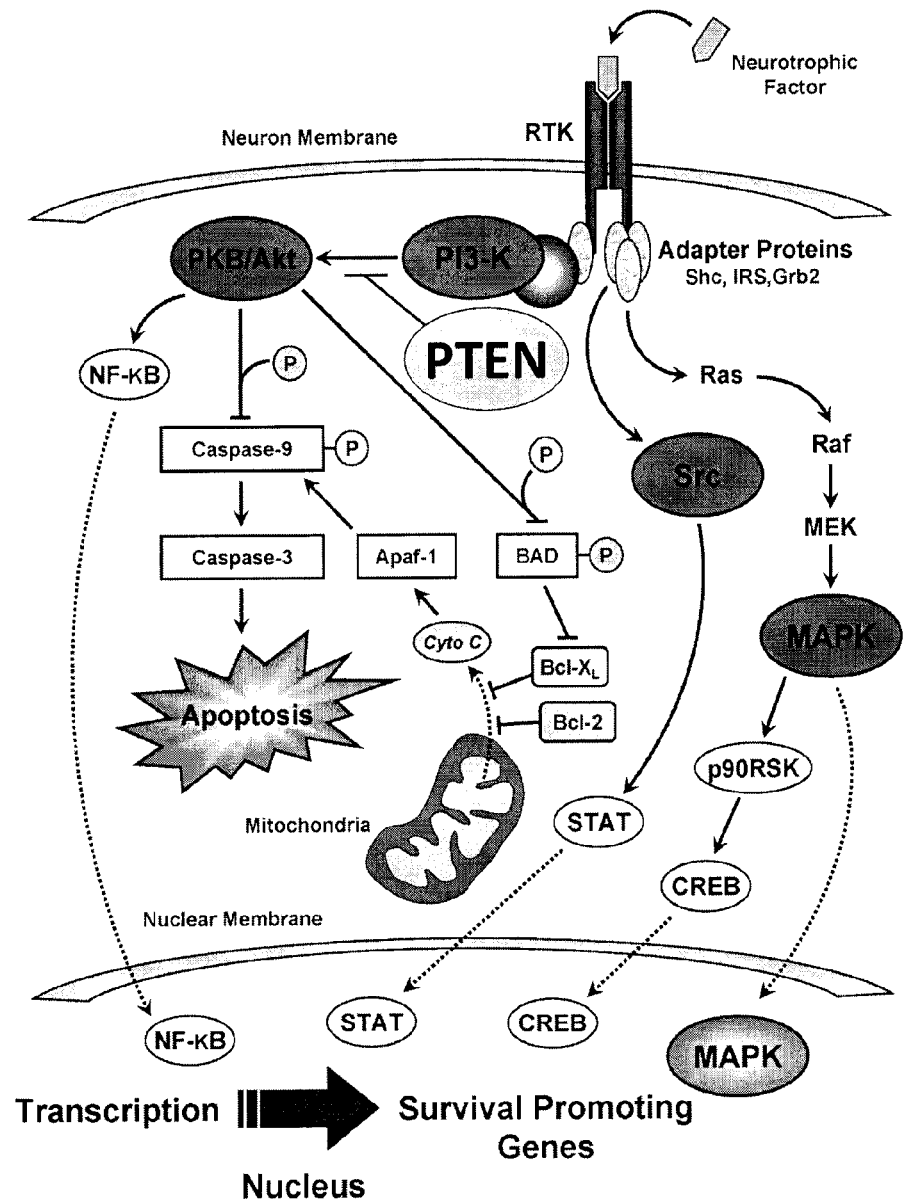
FIG. 4 shows intracellular pathways that inhibit apoptosis. The binding of neurotrophic factors to their specific extracellular receptors results in receptor association and the initiation of intracellular signaling cascades. Important pathways that are activated by growth factors include the mitogen activated protein kinase (MAPK) pathway, the phosphatidylinositide-3 kinase (PI3-K) pathway, and the Src kinase pathway. Activation of MAPK, through an upstream kinase cascade, results in the translocation of MAPK to the nucleus where transcription of survival promoting genes is initiated. MAPK also activates p90RSK, which in turn activates STATs that translocate to the nucleus and alter transcription. PI3-K phosphorylates and activates protein kinase B (PKB also known as Akt). PKB activates the transcription factor NF-κB which translocates to the nucleus and promotes the expression of genes that enhance cell survival. PKB also phosphorylates caspase-9, thereby inactivating it, and preventing the downstream activation of other apoptotic effectors, including caspase-3. The proapoptotic protein BAD is inactivated by phosphorylation, leading to decreased release of cytochrome C from the mitochondria. Src kinase activation leads to STAT activation and STAT mediated transcription of survival promoting genes including bcl-2 and bcl-XL. Key mediators or regulators of apoptosis are labeled in boxes. Dashed arrows indicate the translocation of an intracellular messenger to the nucleus. (Adapted from Koeberle and Bähr, 2004). PTEN phosphatase inhibits PI3K function, thereby preventing important anti-apoptotic signals from being transduced to the nucleus. Furthermore, additional Akt-dependent functions that block apoptosis, downstream of PI3K, are also abolished. Thus, PTEN directly antagonizes PI3K.

The present inventor has shown that several peptides that target protein-protein interactions dependent on C-terminal binding interactions have neuroprotective effects on axotomized retinal ganglion cells (RGCs), and that administration of these peptides provides improvement in RGC function and survival.

Accordingly, in one aspect, the present disclosure provides a method of inhibiting retinal ganglion cell death or dysfunction comprising administering at least one C-terminal peptide to an animal or cell in need thereof. Also included is use of at least one C-terminal peptide for inhibiting retinal ganglion cell death or dysfunction in an animal or cell in need thereof. Further provided is use of at least one C-terminal peptide in the preparation of a medicament for inhibiting retinal ganglion cell death or dysfunction in an animal or cell in need thereof. Even further provided is at least one C-terminal peptide for use in inhibiting retinal ganglion cell death or dysfunction in an animal or cell in need thereof.

In another embodiment, the present disclosure provides a method of inhibiting neuronal cell death or dysfunction comprising administering at least one C-terminal peptide to an animal or cell in need thereof. Also included is use of at least one C-terminal peptide for inhibiting neuronal cell death or dysfunction in an animal or cell in need thereof. Further provided is use of at least one C-terminal peptide in the preparation of a medicament for inhibiting neuronal cell death or dysfunction in an animal or cell in need thereof. Even further provided is at least one C-terminal peptide for use in inhibiting neuronal cell death or dysfunction in an animal or cell in need thereof. In one embodiment, the neuronal cell is a retinal ganglion cell.

In one embodiment, the at least one C-terminal peptide comprises an amino acid sequence as shown in SEQ ID NOs:1-6, 8 or 9 or a variant or analog thereof. In a further embodiment, the at least one C-terminal peptide comprises an amino acid sequence as shown in SEQ ID NOs:1, 2, 5, 6, 8 or 9 or a variant or analog thereof. In another embodiment, at least two, three, four, five or six of the C-terminal peptides are administered or used. In one embodiment, the C-terminal peptides as shown in SEQ ID NOs:1, 2, 5, 6, 8 or 9 or variants or analogs thereof are administered or used. In another embodiment, the C-terminal peptides as shown in SEQ ID NO: 1 or 9 or variants or analogs thereof are administered or used. In another embodiment, the C-terminal peptides as shown in SEQ ID NO: 2 or variants or analogs thereof are administered or used. In another embodiment, the C-terminal peptides as shown in SEQ ID NO:1 and 2 or variants or analogs thereof are administered or used. In yet another embodiment, the C-terminal peptides as shown in SEQ ID NO:9 and 2 or variants or analogs thereof are administered or used. In yet another embodiment, the at least one C-terminal peptide consists of the amino acid sequence as shown in SEQ ID NOs:1-6, 8 or 9.

The term "retinal ganglion cell" or "RGC" as used herein refers to a neuronal cell located near the inner surface of the retina of the eye or isolated therefrom. Retinal ganglion cells transmit processed visual information from the neural retina to the brain, and their axons form the optic nerve.

The phrase "retinal ganglion cell death" as used herein refers to the death of the retinal ganglion cell including without limitation by apoptosis (programmed cell death: PCD), anoikis, necrosis, secondary necrosis, necroptosis/aponecrosis (caspase-independent programmed cell death), parapoptosis, autophagy, excitotoxicity and Wallerian degeneration.

The phrase "retinal ganglion cell dysfunction" as used herein refers to any loss of function of the retinal ganglion cell including without limitation loss of the following functions: electrophysiological properties (ion channel biophysics, channel localization, current expression, gating properties, conductance, electrical summation or integration, action potential firing and propagation, gap-junction coupling or function, hemi-channel expression or function), cellular metabolism, protein biosynthesis (transcription, translation, post-translational modification, folding), protein degradation or recycling, mitochondrial function or energy production, endoplasmic reticulum function, nuclear function (DNA maintenance, DNA repair, DNA transcription), synaptic transmission, synaptic vesicle release, dendritic or axonal connectivity, intracellular transport, axonal transport, somatic or axonal integrity, axon terminal function, axon conductance within the eye or optic nerve, neurotransmitter release, neurotrophic factor release, receptor expression, intracellular signaling, axon myelination and extracellular matrix engagement.

The phrase "neuronal cell death" as used herein refers to the death of a neuronal cell including without limitation by apoptosis (programmed cell death: PCD), anoikis, necrosis, secondary necrosis, necroptosis/aponecrosis (caspase-independent programmed cell death), parapoptosis, autophagy, excitotoxicity and Wallerian degeneration.

The phrase "neuronal cell dysfunction" as used herein refers to any loss of function of the neuronal cell including without limitation loss of the following functions: electrophysiological properties (ion channel biophysics, channel localization, current expression, gating properties, conductance, electrical summation or integration, action potential firing and propagation, gap-junction coupling or function, hemi-channel expression or function), cellular metabolism, protein biosynthesis (transcription, translation, post-translational modification, folding), protein degradation or recycling, mitochondrial function or energy production, endoplasmic reticulum function, nuclear function (DNA maintenance, DNA repair, DNA transcription), synaptic transmission, synaptic vesicle release, dendritic or axonal connectivity, intracellular transport, axonal transport, somatic or axonal integrity, axon terminal function, axon conductance, neurotransmitter release, neurotrophic factor release, receptor expression, intracellular signaling, axon myelination and extracellular matrix engagement.

The phrase "inhibiting retinal ganglion cell death" as used herein refers to increasing the survival of retinal ganglion cells compared to a control that has not been treated with the peptides or compositions disclosed herein. Inhibition includes, without limitation, at least a 5%, 10%, 15%, 20%, 30%, 40%, 50%, 60%, 70%, 80%, 90%, 100%, 200%, 500% or more increase in survival of the retinal ganglion cells compared to the control. The term "control" refers to the absence of treatment or treatment with a negative control, such as TAT-polyA, which does not result in inhibition of retinal ganglion cell death.

The phrase "inhibiting neuronal cell death" as used herein refers to increasing the survival of neuronal cells compared to a control that has not been treated with the peptides or compositions disclosed herein. Inhibition includes without limitation, at least a 5%, 10%, 15%, 20%, 30%, 40%, 50%, 60%, 70%, 80%, 90%, 100%, 200%, 500% or more increase in survival of the neuronal cells compared to the control. The term "control" refers to the absence of treatment or treatment with a negative control, such as TAT-polyA, which does not result in inhibition of neuronal cell death.

The phrase "inhibiting retinal ganglion cell dysfunction" as used herein refers to decreasing the loss of function of retinal ganglion cells compared to a control that has not been treated with the peptides or compositions disclosed herein. Inhibition includes, without limitation, at least a 5%, 10%, 15%, 20%, 30%, 40%, 50%, 60%, 70%, 80%, 90%, 100%, 200%, 500% or more decrease in loss of function of the retinal ganglion cells compared to the control. The term "control" refers to the absence of treatment or treatment with a negative control, such as TAT-polyA, which does not result in inhibition of retinal ganglion cell dysfunction.

The phrase "inhibiting neuronal cell dysfunction" as used herein refers to decreasing the loss of function of neuronal cells compared to a control that has not been treated with the peptides or compositions disclosed herein. Inhibition includes, without limitation, at least a 5%, 10%, 15%, 20%, 30%, 40%, 50%, 60%, 70%, 80%, 90%, 100%, 200%, 500% or more decrease in loss of function of the neuronal cells compared to the control. The term "control" refers to the absence of treatment or treatment with a negative control, such as TAT-polyA, which does not result in inhibition of neuronal cell dysfunction.

In one embodiment, the animal has or is at risk of having a retinal degenerative disorder.

Accordingly, the present disclosure provides a method of treating a retinal degenerative disorder comprising administering at least one C-terminal peptide to an animal or cell in need thereof. Also included is use of at least one C-terminal peptide for treating a retinal degenerative disorder in an animal or cell in need thereof. Further provided is use of at least one C-terminal peptide in the preparation of a medicament for treating a retinal degenerative disorder in an animal or cell in need thereof. Even further provided is at least one C-terminal peptide for use in treating a retinal degenerative disorder in an animal or cell in need thereof. In one embodiment, the at least one C-terminal peptide comprises an amino acid sequence as shown in SEQ ID NOs:1-6, 8 or 9 or a variant or analog thereof. In another embodiment, the at least one C-terminal peptide comprises the amino acid sequence as shown in SEQ ID NOs:1, 2, 5, 6, 8 or 9 or a variant or analog thereof. In a further embodiment, the at least one C-terminal peptide comprises the amino acid sequence as shown in SEQ ID NOs:1 or 9 or a variant or analog thereof. In a further embodiment, the at least one C-terminal peptide comprises the amino acid sequence as shown in SEQ ID NO:2 or a variant or analog thereof. In another embodiment, the at least one C-terminal peptide consists of the amino acid sequence as shown in SEQ ID NOs:1-6, 8 or 9.

The term retinal degenerative disorder as used herein refers to a non-beneficial loss of normal biological function within the retina, caused by, but not limited to, loss of function or cell death of neuronal cells such as retinal ganglion cells, genetic predisposition, acquired disease, sporadic disease development, infectious disease, traumatic injury, central retinal vein occlusion (CRVO), ischemia (stroke), protein or nucleic acid pathology, age-related pathology, tumour (cancer) development, or unknown etiology. In an embodiment, the retinal degenerative disorder is glaucoma (including but not limited to: primary angle closure glaucoma variants, primary open-angle glaucoma variants, and variants of primary glaucoma, developmental glaucoma, and secondary glaucoma), AMD (Age Related Macular Degeneration), retinal ischemia, retinal detachment, diabetic retinopathy, uveoretinitis or vitreoretinopathy, photoreceptor cell dystrophies including but not limited to Leber Congenital Amaurosis (LCA), macular dystrophies, cone-rod dystrophies (CRDs), rod-cone dystrophies (commonly grouped under the term—Retinitis Pigmentosa; RP). In another embodiment, the retinal degenerative disorder is an optic neuropathy or optic atrophy including but not limited to ischemic optic neuropathy, optic neuritis, compressive optic neuropathy, infiltrative optic neuropathy, traumatic optic neuropathy, and mitochondrial optic neuropathies.

In another embodiment, the C-terminal peptide comprises an amino acid sequence as shown in SEQ ID NOs:1, 2, 5, 6, 8 or 9 or a variant or analog thereof and the animal had a stroke, is having a stroke or is at risk of having a stroke (ischemic or hemorrhagic).

Accordingly, the present disclosure provides a method of treating stroke comprising administering at least one C-terminal peptide to an animal or cell in need thereof, wherein the at least one C-terminal peptide comprises an amino acid sequence as shown in SEQ ID NOs:1, 2, 5, 6, 8 or 9 or a variant or analog thereof. Also included is use of at least one C-terminal peptide for treating stroke in an animal or cell in need thereof, wherein the at least one C-terminal peptide comprises an amino acid sequence as shown in SEQ ID NOs:1, 2, 5, 6, 8 or 9 or a variant or analog thereof. Further provided is use of at least one C-terminal peptide in the preparation of a medicament for treating stroke in an animal or cell in need thereof, wherein the at least one C-terminal peptide comprises an amino acid sequence as shown in SEQ ID NOs:1, 2, 5, 6, 8 or 9 or a variant or analog thereof. Even further provided is at least one C-terminal peptide comprising an amino acid sequence as shown in SEQ ID NOs:1, 2, 5, 6, 8 or 9 or a variant or analog thereof for use in treating stroke in an animal or cell in need thereof.

The term "stroke" as used herein refers to the transient or permanent loss of blood supply to cells or a tissue and includes, without limitation, forms of ischemic (loss of blood flow caused by thrombosis (venous or arterial), embolism (venous or arterial), or systemic hypoperfusion)) or hemorrhagic injury (bleeding or compromise of a blood vessel(s) being either intra-axial (intraparenchymal or intraventricular) or extra-axial (subdural, subarachnoid or epidural)) to the retina or central nervous system.

In yet another embodiment, the animal is in need of treatment of CNS insults, such as insults to the brain or spinal cord, including, without limitation, traumatic CNS injury, stroke, concussion, neurodegenerative diseases, and brain damage caused by tumours or surgical procedures.

Accordingly, the present disclosure provides a method of treating CNS insults comprising administering at least one C-terminal peptide to an animal or cell in need thereof. Also included is use of at least one C-terminal peptide for treating CNS insults in an animal or cell in need thereof. Further provided is use of at least one C-terminal peptide in the preparation of a medicament for treating CNS insults in an animal or cell in need thereof. Even further provided is at least one C-terminal peptide for use in treating CNS insults in an animal or cell in need thereof. In one embodiment, the at least one C-terminal peptide comprises an amino acid sequence as shown in SEQ ID NOs:1-6, 8 or 9 or a variant or analog thereof. In one embodiment, the at least one C-terminal peptide comprises an amino acid sequence as shown in SEQ ID NOs:1 or 9 or a variant or analog thereof. In another embodiment, the at least one C-terminal peptide comprises an amino acid sequence as shown in SEQ ID NO: 2 or a variant or analog thereof. In another embodiment, the at least one C-terminal peptide consists of the amino acid sequence as shown in SEQ ID NOs:1-6, 8 or 9.

Recent data demonstrates many clear links between neuronal axon degeneration/regeneration in the peripheral nervous system (PNS) and the central nervous system (CNS). Indeed the cellular inflammatory responses, cytokine and growth factor release, chemokine synthesis, receptor expression in neurons and glial cells, intracellular pathway activation, immune cell recruitment, extracellular matrix alterations, and axon guidance cue-mediated responses appear to be conserved between the two branches of the nervous system, albeit occurring along differing temporal profiles (these responses occur less rapidly in the CNS)(Coleman and Perry 2002; Dezawa 2002; Coleman and Ribchester 2004; Koeberle and Bahr 2004; Vargas and Barres 2007; Gaudet, Popovich et al. 2011; Bosse 2012). Furthermore, both CNS and PNS regeneration are stimulated by similar therapeutic approaches such as the transplantation of Schwann cells or bone marrow stromal cells (Dezawa 2002). Thus, without being limited by theory, it is believed that factors capable of preventing neuron degeneration in the CNS can also prevent the degeneration of neurons and their axons in the PNS, while concurrently promoting axon regeneration.

Thus, the C-terminal peptides disclosed herein are useful in the treatment of PNS insults such as of diabetic neuropathies, amyloid neuropathies, brachial plexus neurophathies, neuralgias, neuritis, nerve compression syndromes, polyneuropathies, peripheral nervous system neoplasms, peripheral pain syndromes. Such diseases are amenable to topical treatment, localized treatment at an injury site, or intravenous treatment.

Accordingly, the present disclosure provides a method of treating PNS insults comprising administering at least one C-terminal peptide to an animal or cell in need thereof. Also included is use of at least one C-terminal peptide for treating PNS insults in an animal or cell in need thereof. Further provided is use of at least one C-terminal peptide in the preparation of a medicament for treating PNS insults in an animal or cell in need thereof. Even further provided is at least one C-terminal peptide for use in treating PNS insults in an animal or cell in need thereof. In one embodiment, the at least one C-terminal peptide comprises an amino acid sequence as shown in SEQ ID NOs:1-6, 8 or 9 or a variant or analog thereof. In one embodiment, the at least one C-terminal peptide comprises an amino acid sequence as shown in SEQ ID NOs:1 or 9 or a variant or analog thereof. In another embodiment, the at least one C-terminal peptide comprises an amino acid sequence as shown in SEQ ID NO: 2 or a variant or analog thereof. In another embodiment, the at least one C-terminal peptide consists of the amino acid sequence as shown in SEQ ID NOs:1-6, 8 or 9.

The term "treatment or treating" as used herein means an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing the disease or condition or preventing the spread of the disease or condition, delay or slowing of disease progression, amelioration or palliation of the disease state, and remission (whether partial or total), whether detectable or undetectable. "Treating" can also mean prolonging survival as compared to expected survival if not receiving treatment.

Other agents or therapeutics can be coadministered or used in combination with the peptides/proteins disclosed herein. Accordingly, in an embodiment, the methods and uses disclosed herein further comprise administering a second CNS therapeutic, including without limitation, a neuroprotective agent, such as latanoprost, neurotrophic factors, such as Nerve Growth Factor (NGF), Brain Derived Neurotrophic Factor (BDNF), Neurotrophin-4/5 (NT-4/5), Neurotrophin-3 (NT-3), Glial cell-line-derived Neurotrophic Factor (GDNF), Neurturin, Artemin, Persephin, Ciliary Neurotrophic Factor (CNTF), Leukemia Inhibitory Factor (LIF), Hepatoma Derived Growth Factor (HDGF), Insulin-like Growth Factors (IGFs), Fibroblast Growth Factors (FGFs), neurotrophic factor analogs, derivatives, or mimetics (e.g. Axokine), NMDA receptor antagonists, AMPA receptor antagonists, kainite receptor antagonists, ion channel blockers, ion channel antagonists, ion channel agonists, Nitric Oxide Synthase inhibitors (iNOS and/or cNOS inhibitors), neuroprotective peptides or peptide derivatives, viral vectors or genetic agents such as plasmids that encode neuroprotective proteins.

The term "C-terminal peptide" as used herein refers to a peptide that is homologous or identical to the C-terminal portion of a protein that is a trigger or effector of cell death and includes the C-terminal peptide of PTEN phosphatase, Kv2.1 voltage-gated potassium channel, Kv1.1 voltage-gated postassium channel, Kv1.3 voltage-gated potassium channel, Kalirin-7, iNOS and Activin receptor II (ActRII). The present examples provide a length of 9 amino acids which was chosen because it confers sufficient specificity for the target proteins. The peptides can be shorter (up to a minimum of the final six C-terminal amino acids), for example, in order to block the C-terminal interaction. Longer sequences that are identical or are similar to the C-terminal of these proteins are also useful. In one embodiment, the C-terminal peptide is at least 6, 7 or 8 amino acids in length. In another embodiment, the peptide is between 6-12 amino acids, optionally 9 amino acids in length. In another embodiment, the at least one C-terminal peptide comprises the amino acid sequences as shown in SEQ ID NOs:1-6, 8 or 9 or variants or analogs thereof (see Table 1). In yet another embodiment, the at least one C-terminal peptide consists of the amino acid sequences as shown in SEQ ID NOs:1-6, 8 or 9.

In an embodiment, the C-terminal peptides are modified for cell permeability, improved stability, and better bioavailability. These modifications include, without limitation, peptide conjugation, peptide cyclization, peptide end modification (e.g. N-acetylation or C-amidation, side chain modifications including the incorporation of non-coded amino acids or non-natural amino acids, N-amide nitrogen alkylation, chirality changes (incorporation of or replacement of L-amino acids with D-amino acids), generation of pseudopeptides (e.g. amide bond surrogates), or peptoids, or azapeptides or azatides). In one embodiment, a protein transduction domain is conjugated to the at least one C-terminal peptide.

The term "protein transduction domain" as used herein refers to a peptide that is able to transfer a larger molecule into a cell. Typical protein transduction domains include, without limitation, domains from TAT (HIV-1-trans-activator gene product), Simian Immunodeficiency Virus (SIV) TAT domain, HSV-1 VP 22 (Herpes Simplex Virus Type 1 tegument protein), poly-arginine sequences (e.g. arginine 9-mer: RRRRRRRRR (SEQ ID NO:11), arginine 8-mer, arginine 6-mer), poly-lysine sequences (e.g. lysine 9-mer: KKKKKKKKK (SEQ ID NO:10), lysine 8-mer, lysine 6-mer), homeoproteins including *Drosophila* Antennapedia (AntpHD) and FTZ (Fushi Tarazu) and En (Engrailed), synthetic cationic protein transduction domains (PTD-4, PTD-5, MST-1 L-R9, Peptide 2, MAP, Pep-1, KALA), Galanin neuropeptide and Galanin derivatives including Transportan, Mastoparan, Human and other species specific homeoproteins (e.g. Hoxa-5, Hox-A4, Hox-B5, Hox-B6, Hox-B7, Hox-D3, Hox-c-8, GAX, MOX-2, Islet-1, cytokines (eg. Interleukin 1-beta, Tumor Necrosis Factor-alpha), Kaposi-Fibroblast Growth Factor (K-FGF or FGF-4) and basic fibroblast growth factors, or chemically synthesized cationic transfection reagents that include Lipofectamine and In vivo Jet. In an embodiment, the protein transduction domain is a TAT protein transduction domain, such as the domain shown in SEQ ID NO: 7 or a variant or analog thereof. In another embodiment, the protein transduction domain is an arginine 9-mer, such as the domain shown in SEQ ID NO:11 or a variant or analog thereof. In yet another embodiment, the protein transduction domain is a lysine 9-mer, such as the domain shown in SEQ ID NO:10 or a variant or analog thereof.

In another aspect, the disclosure provides a C-terminal peptide comprising the amino acid sequence as shown in SEQ ID NOs:1-6, 8 or 9 or a variant or analog thereof. In one embodiment, the C-terminal peptide consists of the amino acid sequence as shown in SEQ ID NOs:1-6, 8 or 9.

In yet another aspect, the present disclosure provides a fusion protein comprising a protein transduction domain conjugated to a C-terminal peptide. In one embodiment, the C-terminal peptide comprises an amino acid sequence as shown in SEQ ID NOs:1-6, 8 or 9 or a variant or analog thereof. In another embodiment, the C-terminal peptide consists of an amino acid sequence as shown in SEQ ID NOs:1-6, 8 or 9.

It will be appreciated that the disclosure includes amino acid molecules comprising amino acid sequences having substantial sequence identity with the amino acid sequences of the C-terminal peptides or TAT protein transduction domain, such as the amino acid sequences shown in SEQ ID NOs:1-6, 8 or 9. The term "sequences having substantial sequence identity" means those amino acid sequences that have slight or inconsequential sequence variations from these sequences, i.e., the sequences function in substantially the same manner to produce functionally equivalent peptides. The variations may be attributable to local mutations or structural modifications.

Amino acid sequences having substantial identity include amino acid sequences having at least about 50 percent identity with a protein having an amino acid sequence as shown in SEQ ID NOs: 1-6, 8 or 9. The level of sequence identity, according to various aspects of the disclosure is at least about: 60, 70, 75, 80, 83, 85, 88, 90, 93, 95 or 98 percent. Methods for aligning the sequences to be compared and determining the level of homology between the sequences are described in detail above.

Sequence identity can be calculated according to methods known in the art. Sequence identity is most preferably assessed by the algorithm of BLAST version 2.1 advanced search. BLAST is a series of programs that are available, for example, online from the National Institutes of Health. The advanced blast search is set to default parameters. (ie Matrix BLOSUM62; Gap existence cost 11; Per residue gap cost 1; Lambda ratio 0.85 default). References to BLAST searches are: Altschul, S. F., Gish, W., Miller, W., Myers, E. W. & Lipman, D. J. (1990) "Basic local alignment search tool." J. Mol. Biol. 215:403410; Gish, W. & States, D. J. (1993) "Identification of protein coding regions by database similarity search." Nature Genet. 3:266272; Madden, T. L., Tatusov, R. L. & Zhang, J. (1996) "Applications of network BLAST server" Meth. Enzymol. 266:131_141; Altschul, S. F., Madden, T. L., Schïffer, A. A., Zhang, J., Zhang, Z., Miller, W. & Lipman, D. J. (1997) "Gapped BLAST and PSI_BLAST: a new generation of protein database search programs." Nucleic Acids Res. 25:33893402; Zhang, J. & Madden, T. L. (1997) "PowerBLAST: A new network BLAST application for interactive or automated sequence analysis and annotation." Genome Res. 7:649656.

Analogs of the peptides having the amino acid sequences shown in SEQ ID NOs:1-6, 8 or 9 as described herein, may include, but are not limited to an amino acid sequence containing one or more amino acid substitutions, insertions, and/or deletions. Amino acid substitutions may be of a conserved or non-conserved nature. Conserved amino acid substitutions involve replacing one or more amino acids of the proteins of the disclosure with amino acids of similar charge, size, and/or hydrophobicity characteristics. When only conserved substitutions are made the resulting analog should be functionally equivalent. Non-conserved substitutions involve replacing one or more amino acids of the amino acid sequence with one or more amino acids which possess dissimilar charge, size, and/or hydrophobicity characteristics.

Without the intention of being limited thereby, in one embodiment, the substitutions of amino acids are made that preserve the structure responsible for the ability to competitively inhibit the target protein or transport proteins as disclosed herein. Conservative substitutions are described in the patent literature, as for example, in U.S. Pat. No. 5,264,558. It is thus expected, for example, that interchange among non-polar aliphatic neutral amino acids, glycine, alanine, proline, valine and isoleucine, would be possible. Likewise, substitutions among the polar aliphatic neutral amino acids, serine, threonine, methionine, asparagine and glutamine could possibly be made. Substitutions among the charged acidic amino acids, aspartic acid and glutamic acid, could probably be made, as could substitutions among the charged basic amino acids, lysine and arginine. Substitutions among the aromatic amino acids, including phenylalanine, histidine, tryptophan and tyrosine would also likely be possible. Other substitutions might well be possible.

One or more amino acid insertions may be introduced into the amino acid sequences shown in SEQ ID NOs: 1-6, 8 or 9. Amino acid insertions may consist of single amino acid residues or sequential amino acids ranging from 2 to 15 amino acids in length. Such variant amino acid molecules can be readily tested for competitive inhibition with the target protein or protein transport activity.

Deletions may consist of the removal of one or more amino acids, or discrete portions from the amino acid sequence shown in SEQ ID NOs: 1-6, 8 or 9. The deleted amino acids may or may not be contiguous. The lower limit length of the resulting analog with a deletion mutation is at least 6, 7 or 8 amino acids.

Exemplary methods of making the alterations set forth above are disclosed by Sambrook et al (Molecular Cloning: A Laboratory Manual, 2nd Ed., Cold Spring Harbor Laboratory Press, 1989).

The peptides described above (including truncations, analogs, etc.) may be prepared using recombinant DNA methods. These peptides may be purified and/or isolated to various degrees using techniques known in the art. Accordingly, nucleic acid molecules having a sequence which encodes a peptide of the disclosure may be incorporated according to procedures known in the art into an appropriate expression vector which ensures good expression of the protein. Possible expression vectors include but are not limited to cosmids, plasmids, or modified viruses (e.g., replication defective retroviruses, adenoviruses and adeno-associated viruses), so long as the vector is compatible with the host cell used. The expression "vectors suitable for transformation of a host cell", means that the expression vectors contain a nucleic acid molecule encoding a peptide of the disclosure and regulatory sequences, selected on the basis of the host cells to be used for expression, which are operatively linked to the nucleic acid molecule. "Operatively linked" is intended to mean that the nucleic acid is linked to regulatory sequences in a manner which allows expression of the nucleic acid.

The disclosure therefore also includes nucleic acids that encode the peptides and fusion proteins described herein.

The disclosure further contemplates a recombinant expression vector of the disclosure containing a nucleic acid molecule that encodes a peptide or fusion protein of the disclosure and the necessary regulatory sequences for the transcription and translation of the inserted protein-sequence.

The recombinant expression vectors of the disclosure may also contain a selectable marker gene that facilitates the selection of host cells transformed or transfected with a recombinant molecule of the disclosure. Examples of selectable marker genes are genes encoding a protein which confers resistance to certain drugs, such as G418 and hygromycin.

Recombinant expression vectors can be introduced into host cells to produce a transformed host cell. The term "transformed host cell" is intended to include prokaryotic and eukaryotic cells which have been transformed or transfected with a recombinant expression vector of the disclosure. The terms "transformed with", "transfected with", "transformation" and "transfection" are intended to encompass introduction of nucleic acid (e.g. a vector) into a cell by one of many possible techniques known in the art.

Suitable host cells include a wide variety of prokaryotic and eukaryotic host cells. For example, the proteins of the disclosure may be expressed in bacterial cells such as E. coli, insect cells (using baculovirus), yeast cells or mammalian cells, COS1 cells. Other suitable host cells can be found in Goeddel, Gene Expression Technology: Methods in Enzymology 185, Academic Press, San Diego, Calif. (1991).

Alternatively, the peptides or fusion proteins can be prepared by chemical synthesis using techniques well known in the chemistry of proteins such as solid phase synthesis [Merrifield 1964] or synthesis in homogeneous solution [Houbenwycl, 1987].

The term "administering a C-terminal peptide" or "administering a fusion protein" includes both the administration of the peptide/protein as well as the administration of a nucleic acid sequence encoding the peptide/protein to an animal or to a cell in vitro or in vivo. The term "administering" also includes the administration of a cell that expresses the peptide/protein.

The peptides/proteins described herein may be administered in vivo or ex vivo to a cell which is then administered. For example, cells may be transformed or transduced with the nucleic acid encoding the peptide/protein described herein and then the cells are administered in vivo. In one embodiment, the cells are retinal ganglion cells or neurons.

The term "a cell" includes a single cell as well as a plurality or population of cells.

Administration of an "effective amount" of the peptides/proteins and nucleic acids or cells in the methods and uses of the present disclosure is defined as an amount effective, at dosages and for periods of time necessary to achieve the desired result. The effective amount of the peptide/protein or nucleic acid or cells of the disclosure may vary according to factors such as the disease state, age, sex, and weight of the animal. Dosage regimens may be adjusted to provide the optimum therapeutic response. For example, several divided doses may be administered daily or the dose may be proportionally reduced as indicated by the exigencies of the therapeutic situation. The mode of administration (e.g. in vivo by injection or ex vivo in culture) will also impact the dosage regime.

The at least one C-terminal peptide, fusion protein or compositions thereof may be administered or used in the methods disclosed herein in any manner, including without limitation, intravenously, intraocularly, via optic nerve injection, topically, intraperitoneally, via surgical implantation, for example, by implanting a delivery device, intrathecally, or via injection directly into the CNS tissue (including brain or spinal cord).

The term "animal" as used herein includes all members of the animal kingdom including humans.

The disclosure further includes pharmaceutical compositions containing the peptides/proteins or nucleic acids or cells described herein for use in inhibiting retinal ganglion cell death or treating a retinal degenerative disorder or stroke.

Such pharmaceutical compositions can be for any use, including without limitation, intravenously, intraocularly, via optic nerve injection, topically, intraperitoneally, via surgical implantation, for example, by implantation of a delivery device, intrathecally, or via injection directly into the CNS tissue (including brain or spinal cord).

The pharmaceutical compositions and/or the C-terminal peptides and fusion proteins described herein can be for use topically. In one embodiment a pharmaceutical composition comprising at least one C-terminal peptide, wherein the C-terminal peptide comprises an amino acid sequence as shown in SEQ ID NOs:1, 2, 3, 5, 6, 8 or 9 or a variant or analog thereof is applied topically to the eye, for example via eye drops or a topical ointment or liquid. Optionally, the pharmaceutical composition comprising at least one C-terminal peptide, wherein the C-terminal peptide comprises an amino acid sequence as shown in SEQ ID NOs:1, 2, 3, 5, 6, 8 or 9 or a variant or analog thereof is for use in the form of eye drops which can be administered to a subject in need thereof.

The pharmaceutical compositions of the disclosure are intended for administration to humans or animals or cells or tissue in culture. Dosages to be administered depend on individual needs, on the desired effect and on the chosen route of administration.

The pharmaceutical compositions can be prepared by per se known methods for the preparation of pharmaceutically acceptable compositions which can be administered to patients, and such that an effective quantity of the active substance is combined in a mixture with a pharmaceutically acceptable vehicle. Suitable vehicles are described, for example, in Remington's Pharmaceutical Sciences (Remington's Pharmaceutical Sciences, Mack Publishing Company, Easton, Pa., USA 2003—20$^{th}$ Edition) and in The United States Pharmacopeia: The National Formulary (USP 24 NF19) published in 1999).

On this basis, the pharmaceutical compositions include, albeit not exclusively, the active compound or substance in association with one or more pharmaceutically acceptable vehicles or diluents, and contained in buffered solutions with a suitable pH and iso-osmotic with the physiological fluids. In one embodiment, the pharmaceutically acceptable vehicle or diluent is sterile phosphate buffered saline, sterile saline, or purified water. The pharmaceutical compositions may additionally contain other agents such as those disclosed herein as second CNS therapeutics.

Accordingly, the present disclosure provides a composition comprising at least one C-terminal peptide and a pharmaceutically acceptable carrier, wherein the C-terminal peptide comprises the amino acid sequence as shown in SEQ ID NOs:1-6, 8 or 9 or a variant or analog thereof. In one embodiment, the composition comprises at least one C-terminal peptide and a pharmaceutically acceptable carrier, wherein the C-terminal peptide comprises the amino acid sequence as shown in SEQ ID NOs:1, 2, 5, 6, 8 or 9 or a variant or analog thereof.

In another embodiment, the composition comprises at least one C-terminal peptide and a pharmaceutically acceptable carrier, wherein the C-terminal peptide comprises the amino acid sequence as shown in SEQ ID NOs:1, 2, 5, 6, 8 or 9 or a variant or analog thereof. In another embodiment, the composition comprises at least one C-terminal peptide and a pharmaceutically acceptable carrier, wherein the C-terminal peptide comprises the amino acid sequence as shown in SEQ ID NOs:1 or 9 or a variant or analog thereof. In yet another embodiment, the composition comprises at least one C-terminal peptide and a pharmaceutically acceptable carrier, wherein the C-terminal peptide comprises the amino acid sequence as shown in SEQ ID NO: 2 or a variant or analog thereof.

The composition optionally comprises at least two C-terminal peptides, wherein each C-terminal peptide comprises the amino acid sequence as shown in SEQ ID NOs:1-6, 8 or 9 or a variant or analog thereof. In one embodiment, the at least two C-terminal peptides comprise the C-terminal peptide as shown in SEQ ID NO:1 and the C-terminal peptide as shown in SEQ ID NO:2. In another embodiment, the at least two C-terminal peptides comprise the C-terminal peptide as shown in SEQ ID NO:9 and the C-terminal peptide as shown in SEQ ID NO:2. In another embodiment, the composition comprises at least 3 or at least 4 or at least 5 or at least 6 C-terminal peptides, wherein each C-terminal peptide is selected from the peptides as shown in SEQ ID NOs:1-6, 8 or 9 or a variant or analog thereof. In an embodiment, the at least one C-terminal peptide consists of the amino acid sequence as shown in SEQ ID NOs:1-6, 8 or 9.

In another embodiment, the present disclosure provides a composition comprising at least one fusion protein and a pharmaceutically acceptable carrier, wherein the at least one fusion protein comprises a protein transduction domain conjugated to a C-terminal peptide. The composition optionally comprises at least two fusion proteins, wherein each fusion protein comprises a protein transduction domain conjugated to a C-terminal peptide. In another embodiment, the composition comprises at least 3 or at least 4 or at least 5 or at least 6 fusion proteins, wherein each fusion protein comprises a protein transduction domain conjugated to a C-terminal peptide. In one embodiment, the C-terminal peptide comprises the amino acid sequence as shown in SEQ ID NOs:1-6, 8 or 9 or a variant or analog thereof. In another embodiment, the C-terminal peptide consists of the amino acid sequence as shown in SEQ ID NOs:1-6, 8 or 9.

In an embodiment, the protein transduction domain is TAT, K9, or R9 as shown in SEQ ID NO:7, 10 or 11 or a variant or analog thereof.

In one embodiment, there is provided a composition comprising at least two fusion proteins, wherein the first fusion protein comprises TAT conjugated to the C-terminal peptide as shown in SEQ ID NO:1 or 9 or a variant or analog thereof and the second fusion protein comprises TAT conjugated to the C-terminal peptide as shown in SEQ ID NO:2 or a variant or analog thereof.

The above disclosure generally describes the present application. A more complete understanding can be obtained by reference to the following specific examples. These examples are described solely for the purpose of illustration and are not intended to limit the scope of the disclosure. Changes in form and substitution of equivalents are contemplated as circumstances might suggest or render expedient. Although specific terms have been employed herein, such terms are intended in a descriptive sense and not for purposes of limitation.

The following non-limiting examples are illustrative of the present disclosure:

EXAMPLES

Results

Figure 5:
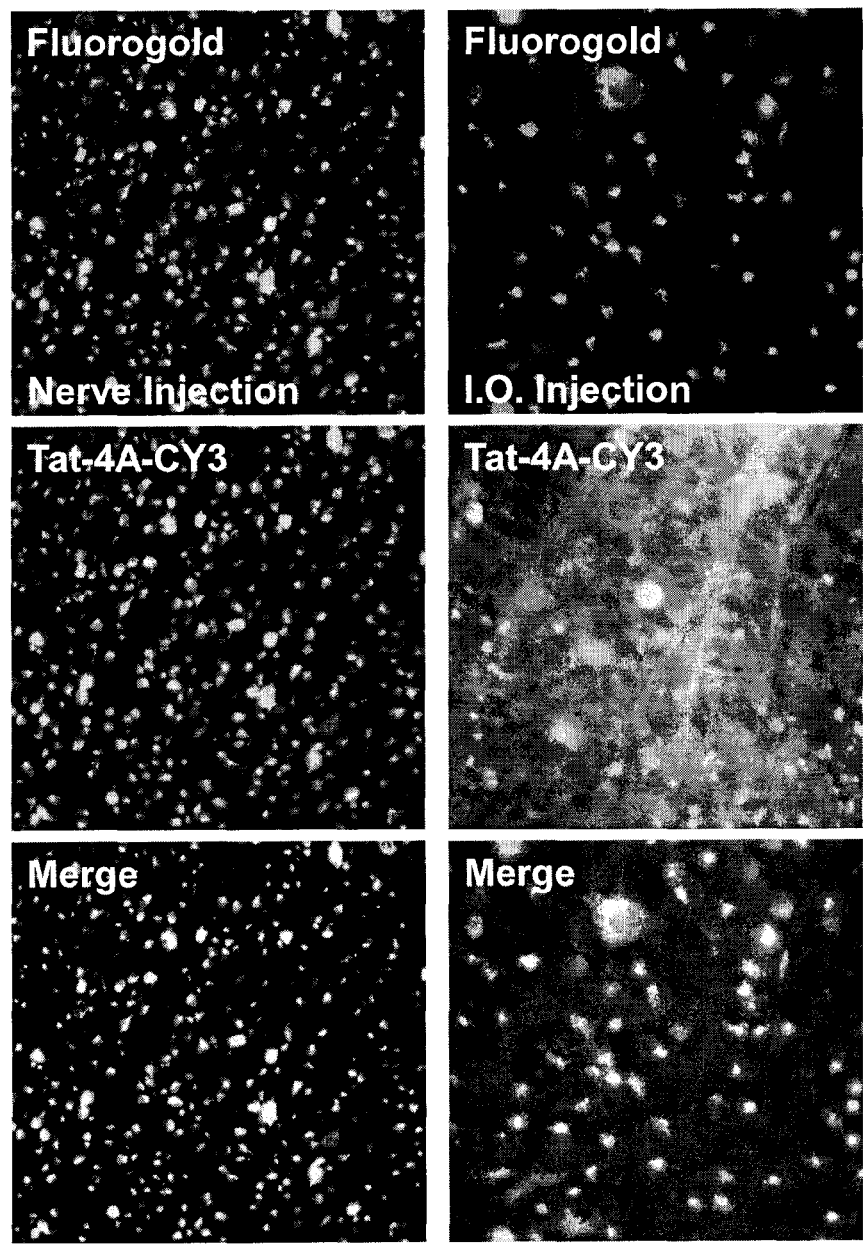
FIG. 5 shows Retinal Cy3-Tat-4A Labeling. Epifluorescence images showing the cellular localization of Cy3-labeled Tat-4A peptide following injection into the optic nerve (images on left) or intraocular injection (images on right). Nerve injection resulted in the selective transfection of axotomized retinal ganglion cells that were retrogradely labeled with Fluorogold from their target, the superior colliculus (colocalization shown in merged image at bottom). Intraocular injection resulted in the widespread transfection of the inner retina as evidence by labeling of retinal ganglion cells, surrounding glia, and other neurons in the ganglion cell layer. Retinal ganglion cells were pre-labeled with Fluorogold prior to intraocular injection of Cy3-labeled peptide.

TAT-conjugated, Cy3-labeled peptides were initially injected in order to determine their cellular localization after delivery by two routes: injection into the transected optic nerve, or intraocular injection (FIG. 5). Injection of labeled peptides into the transected optic nerve stump selectively transfected axotomized RGCs (FIG. 5, left panel). In contrast, intraocular injection transfected RGCs in addition to surrounding glial cells and other neurons in the ganglion cell layer (FIG. 5, right panel). This technique produced widespread transfection of the entire inner retina. Thus, these two drug delivery approaches allowed testing of the effects of the peptides selectively on injured RGCs (via nerve injection) or globally within the tissue (via intraocular injection). This is important because glial cells and local immune cells (microglia) are known to contribute to RGC apoptosis after injury, meaning that the peptides may have additional benefits by acting indirectly through these cells.

Figure 6:
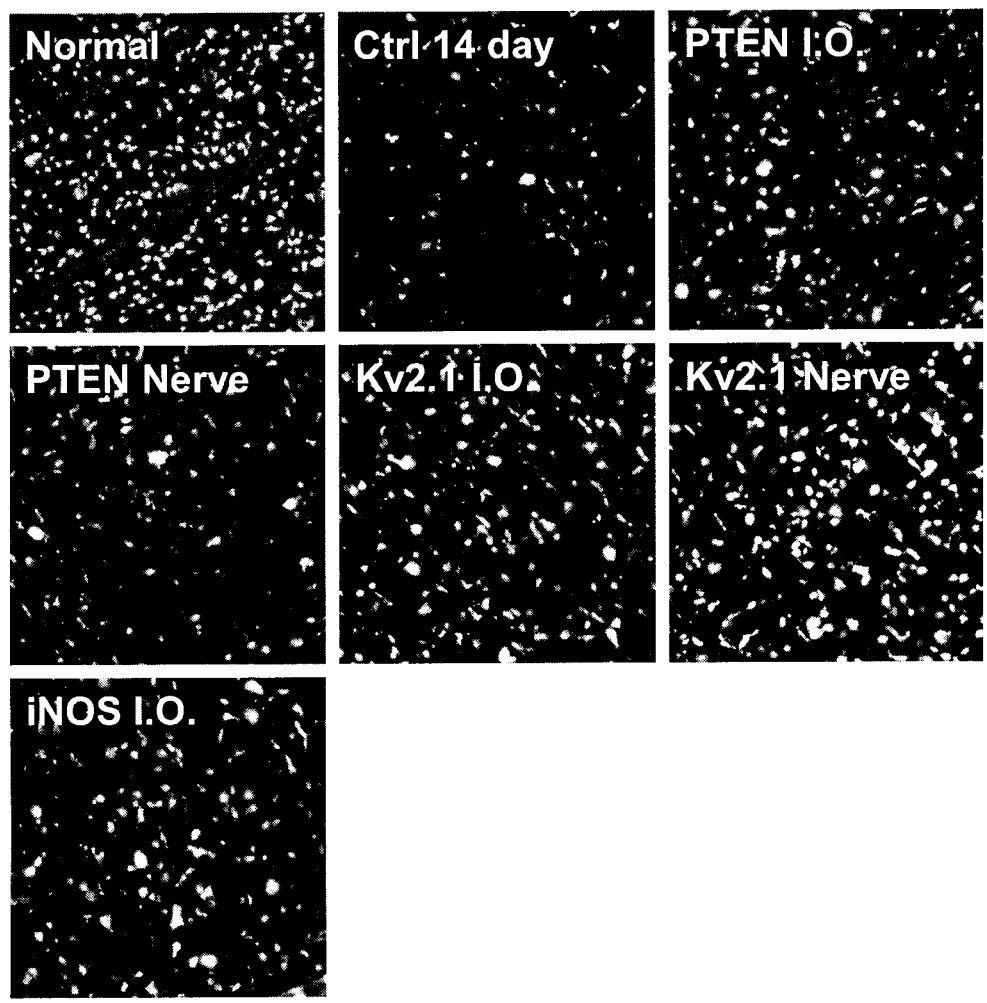
FIG. 6 shows Flatmounted retinas of Fluorogold retrogradely labeled retinal ganglion cells. Epifluorescence images labeled RGCs in a normal (unlesioned) eye (top left), or at 14 days postaxotomy (Ctrl 14 day). Intraocular (I.O.) or nerve injection of PTEN or Kv2.1 peptides increased RGC survival compared to controls at 14 days postaxotomy. iNOS peptides also increased RGC survival via intraocular delivery. Animals received two intraocular injections of peptides at day 3 or day 8 after axotomy. Nerve injected animals received only a single injection at the time of axotomy. All peptides were injected at a concentration of 10 mg/ml.

Next, the potential therapeutic effects of specific peptides that targeted C-terminal interactions with proteins that orchestrate apoptosis were tested. One of these peptides targeted C-terminal interactions of PTEN phosphatase (TAT-PTEN). This peptide was delivered via intraperitoneal injections (IP), intraocular injections (IO), or injections into the optic nerve, following optic nerve transection. RGC densities were quantified from fixed, flat-mounted retinas at 14 days postaxotomy. IP injections of TAT-PTEN (500 µg per injection) or intraocular injections (1 mg/ml) at 3 days and 8 days postaxotomy did not noticeably affect RGC survival relative to control vehicle injection (Ctrl; FIG. 7A). At 10 mg/ml, intraocular injection of TAT-PTEN produced a robust increase in RGC survival (FIG. 6, 7A). Nerve injection of TAT-PTEN (10 mg/ml) also enhanced RGC survival by ~2-fold (FIG. 6, 7A). These results show that TAT-PTEN is an effective anti-apoptotic therapeutic for injured RGCs, and that additional benefits are derived from globally targeting the retina via intraocular injections.

The second peptide targets the C-terminal interactions of the potassium channel Kv2.1, which has been shown to contribute specifically to neuronal apoptosis (Pal, Hartnett et al. 2003; Pal, Takimoto et al. 2006; Redman, He et al. 2007; Aras, Saadi et al. 2009). TAT-Kv2.1 produced the greatest increase in RGC survival that was observed by the present inventor with any single treatment. Nerve injection of TAT-Kv2.1 (FIG. 6, 7B) increased RGC survival by 5-fold compared to controls (~80% of the normal density of 2500 cells/mm$^2$). Furthermore, intraocular injection produced a 3-fold survival increase (FIG. 6, 7B). It has been shown that neurons selectively express Kv2.1 channels when undergoing apoptosis (Pal, Hartnett et al. 2003; Pal, Takimoto et al. 2006; Redman, He et al. 2007; Aras, Saadi et al. 2009), hence the reason why the selective targeting of Kv2.1 in RGCs (via nerve injection) showed higher efficacy in this case.

Figure 9:
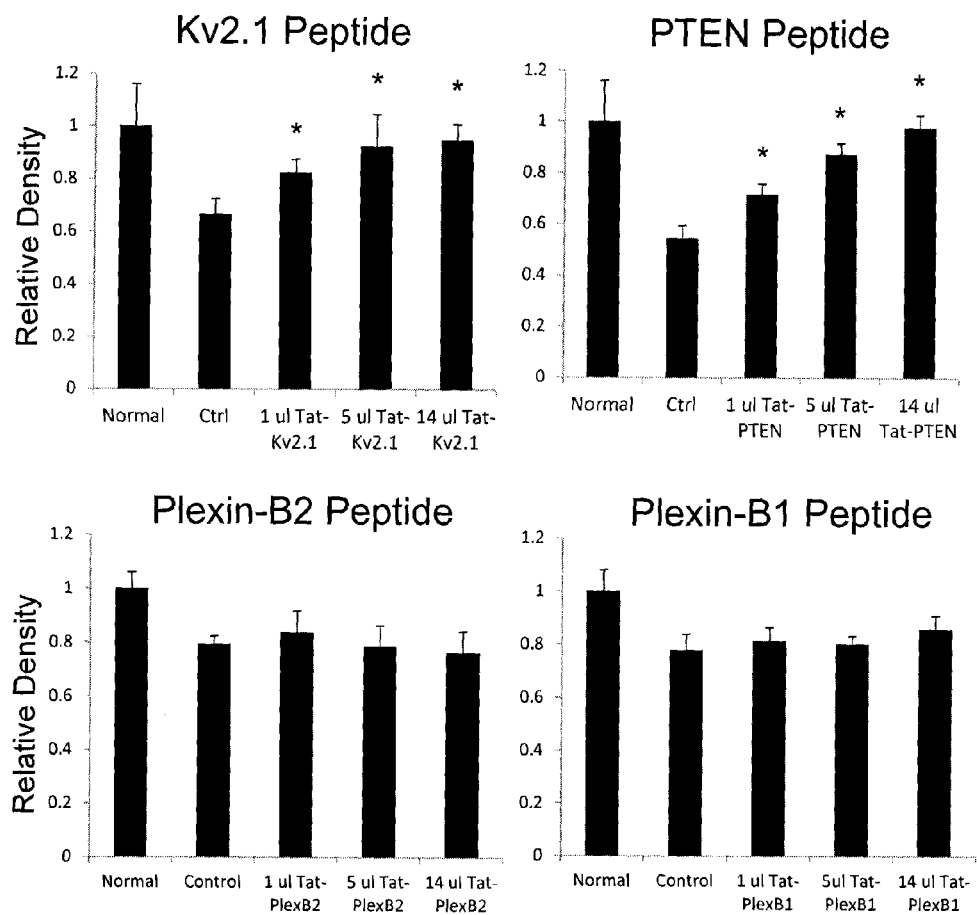
FIG. 9 shows quantification of cortical neuron survival after glutamate delivery. Post-natal cortical neurons were cultured for 2 weeks to allow neurite development. Cells were killed by adding 5 mM glutamate to their medium for 24 hours. Controls also received vehicle in the medium, whereas treatment groups also received increasing volumes of each peptide from a stock solution (10 mg/ml). Cell survival was quantified using a crystal violet survival assay, with a count from each well derived by a plate reader. Survival is expressed relative to normal cells that did not receive glutamate (normal). The vertical axis represents the mean optical density (±SEM) relative to normal, untreated cells. Higher optical densities indicate greater cell numbers. TAT-Kv2.1 and TAT-PTEN increased cell survival at 24 hours (TOP), whereas TAT-Plexin-B2 or TAT-Plexin-B1 peptides did not. *=$p<0.05$ relative to control.

Additionally, other peptides were identified that showed varying degrees of neuroprotection, and some peptides that did not have any effect. For example, the delivery of peptides that target C-terminal interactions of inducible nitric-oxide synthase (iNOS), produced a 2-fold increase in cell survival when delivered via intraocular injections, however little or no effect was observed after IP or nerve delivery (FIG. 7C). Intraocular and nerve injections of TAT-conjugated polyalanine control peptides (TAT-4A) were used as additional controls (FIG. 7D). Neither intraocular nor nerve delivery of control peptides produced any difference in axotomized RGC survival at 14 days. Following these results, these peptides were tested in additional injury paradigms. Intravenous TAT-PTEN or TAT-Kv2.1 (500 µg at 1 day and 8 days after injury) significantly enhanced RGC survival following optic nerve ligation (FIG. 8), demonstrating benefits for ischemic (stroke) injury in the CNS. This is important because ischemic injury has been implicated as one of the factors that results in RGC apoptosis in glaucoma (Osborne, Melena et al. 2001; Nakabayashi 2004; Schmidt, Pillunat et al. 2004; Toda and Nakanishi-Toda 2007). Studies were also performed on cultured post-natal cortical neurons. Neurons were killed with the excitotoxin glutamate, which is known to contribute to neuronal death after trauma or stroke in the adult CNS, and in glaucoma (Arundine and Tymianski 2004; Johnston 2005; Hazell 2007; Seki and Lipton 2008). Both treatments showed a dose-dependent survival-promoting effect on cultured cortical neurons at 24 hours following glutamate exposure, whereas peptides that target Plexins had no effect (FIG. 9). Overall, this data points to promising therapeutic potential for the novel peptides in preventing RGC death in visual disease.

Figure 10:
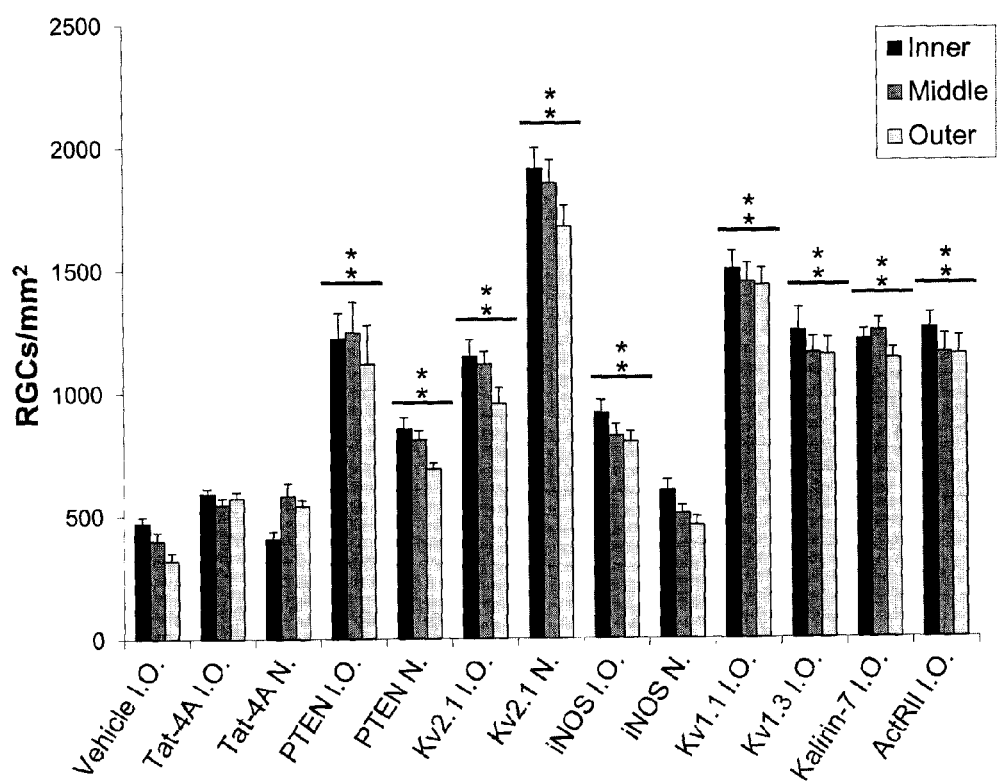
FIG. 10 shows optic nerve transection results. Intraocular (I.O.), or nerve (N.) injections of peptides were delivered after optic nerve transection. I.O. injections were made at 3 and 8 days after injury, whereas the nerve injection was made at the time of axotomy. RGC survival was quantified at 14 days after injury. Controls were vehicle or a non-functional TAT-conjugated peptide (TAT-4A). **=$p<0.01$ relative to the corresponding control. Controls were intraocularly injected vehicle (vehicle I.O.), intraocularly injected Tat-4A (Tat-4A I.O.), or nerve injected Tat-4a (Tat-4A N).

The effects of other C-terminal peptides were then tested in the well-established optic nerve transection model (FIG. 10). Peptides that match the C-terminal sequences of the voltage-gated potassium channels Kv1.1 and Kv1.3, or proteins Kalirin-7, and Activin Receptor II (ActRII) all significantly enhanced RGC survival when delivered by intraocular injection (FIG. 10). These peptides target distinct aspects of neuron apoptosis and can be delivered alone or in combination with one another to enhance cell survival and custom-tailor therapeutics for different types of CNS disease or injury.

Figure 11:
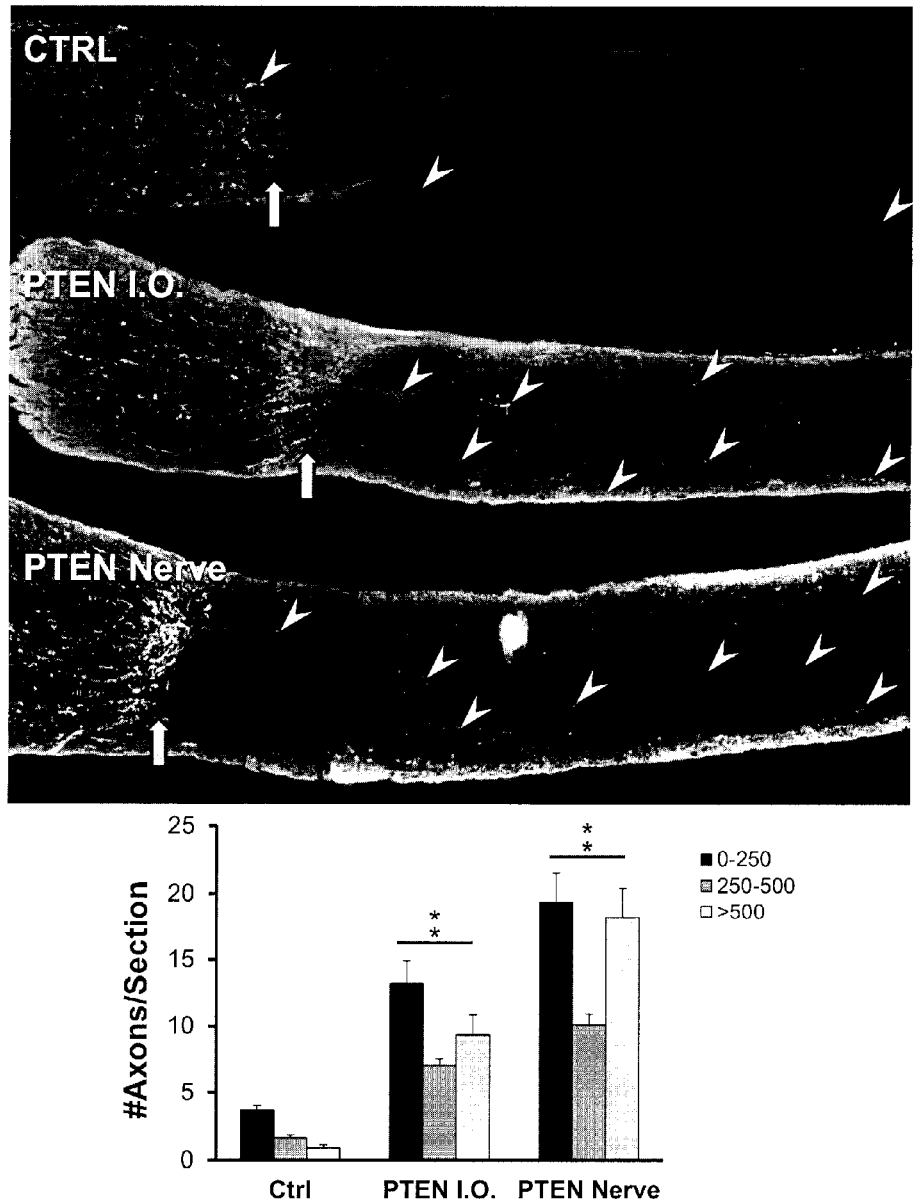
FIG. 11 shows the quantification of axon regeneration after optic nerve crush. The upper black panel consists of composite images of epifluorescence micrographs showing GAP-43 immunostaining in longitudinal sections of optic nerve at 21 days after optic nerve crush. Control nerves (top; intraocular injection of vehicle) showed few regenerating axons (arrowheads) distal to the crush site (vertical arrow); whereas robust retinal ganglion cell (RGC) axon regeneration (arrowheads) was observed after intraocular injection of PTEN C-terminal peptide (PTEN I.O.: middle image) or application of PTEN C-terminal peptide at the crush site via a soaked piece of gel-foam (PTEN Nerve: bottom image). The crush site in each nerve is marked by a vertical arrow, and the retina (not visible) is located beyond the left hand side of each image; the brain target of the regenerating axons is located beyond the right hand side of the image. Bottom: Graph represents the quantification of the average number of regenerating axons per optic nerve section (±SEM) at different distances from the crush site. The number of axons was quantified in three different bins (<250 μm, 250-500 μm, or >500 μm). *=$p<0.01$, relative to control.

Factors that promote neuron cell survival can also promote axon regeneration (Koeberle and Bahr 2004). This is important because axon regrowth can re-establish functional connectivity between different regions of the nervous system, thereby contributing to the recovery of function after disease, injury, or insult states. Thus, it is predicted that the peptides described herein will also be useful in the promotion of axon regeneration in the injured nervous system. In order to test this, the optic nerve crush model was used: the optic nerve is crushed rather than cut, which allows study of the regeneration of injured retinal ganglion cells (RGCs) (Misantone, Gershenbaum et al. 1984; Barron, Dentinger et al. 1986; Stevenson 1987; Sautter and Sabel 1993). A TAT-conjugated PTEN C-terminal peptide was delivered via intraocular injections, or via a piece of gel-foam wrapped around the crush site of the optic nerve. Both of these experimental interventions significantly enhanced axon regeneration by RGCs at 21 days after optic nerve crush, as shown in FIG. 11. As both PTEN I.O. and PTEN Nerve treatments significantly increased the number of regenerating axons in all three bins of the distal optic nerve, it is shown that the described C-terminal peptides can promote axon regeneration.

These findings establish that the PTEN peptide promotes axon regeneration in adult mammals, which would be useful in treating any form of central or peripheral neuropathy or spinal cord injury. It is expected that the other survival promoting peptides described herein would similarly be useful in promoting axon regeneration.

Figure 12:
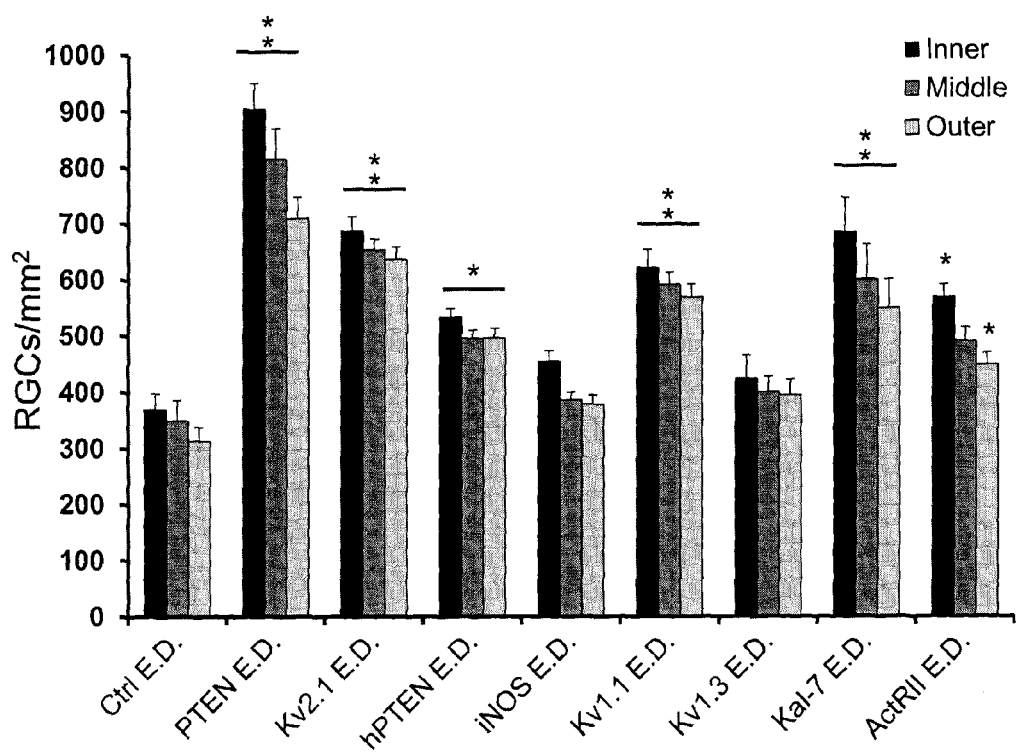
FIG. 12 shows the quantification of retinal ganglion cell (RGC) survival after eye drop delivery of C-terminal peptides. Arginine 9-mer-conjugated C-terminal peptides were delivered via eye drops (E.D.), once per day, at day 1, 2, 3, 4, 5, 6, and 7 after cutting the optic nerve (Axotomy). Retinal ganglion cell (RGC) survival was quantified at 14 days after axotomy, showing that C-terminal PTEN, Kv2.1, human PTEN (hPTEN), Kv1.1, Kalirin-7 (Kal-7), and Activin Receptor II (ActRII) peptides significantly increased RGC survival. Graph shows mean RGC densities ±SEM, at three different retinal eccentricities: inner, middle, outer: **=$p<0.01$ relative to control, *=$p<0.05$ relative to control. Controls were sterile saline eye drops (Ctrl E.D.).

Eye drops are a clinically relevant method of non-invasive therapeutic delivery to the injured retina. Using this method it has recently been demonstrated that large proteins and small synthetic compounds can be topically delivered to the retina, enhancing retinal ganglion cell survival after axotomy, ischemia, excitotoxic NMDA application, or elevated intraocular pressure in glaucoma models (Aviles-Trigueros, Mayor-Torroglosa et al. 2003; Metoki, Ohguro et al. 2005; Seki, Tanaka et al. 2005; Danylkova, Alcala et al. 2007; Kim, Chang et al. 2007; Goldenberg-Cohen, Dadon-Bar-El et al. 2009; Kanamori, Naka et al. 2009; Lambiase, Aloe et al. 2009; Hong, Kim et al. 2010; Colafrancesco, Parisi et al. 2011). Thus, the effects of the C-terminal peptides described herein on the survival of axotomized retinal ganglion cells (RGCs) were tested. Arginine 9-mer (R9: RRRRRRRRR-)-conjugated C-terminal peptides were delivered via eye drops, once per day, at day 1, 2, 3, 4, 5, 6, and 7 after cutting the optic nerve. RGC survival was quantified at 14 days after axotomy, showing that C-terminal PTEN, Kv2.1, human PTEN (hPTEN), Kv1.1, Kalirin-7 (Kal-7), and Activin Receptor II (ActRII) peptides significantly enhanced RGC survival (FIG. 12). These findings show that the C-terminal peptide therapeutics promote injured retinal neuron survival and can be used to treat eye/retinal disorders, injuries, insults, or diseases via topical application such as eye drop application.

Stroke is one of the leading causes of death world-wide. Since our C-terminal peptides prevent neurodegeneration, the effects of these therapeutics after stroke of the middle cerebral artery were tested in adult rats. Middle Cerebral Artery Occlusion (MCAO) is a well-accepted stroke model in experimental animals. To test the C-terminal peptides described herein, an improved thromboembolic model of MCAO was used, where an autologous blood clot is injected into the origin of the middle cerebral artery in rats, producing an infarct (region of brain degeneration) that closely mimics stroke observations in humans (Wang, Yang et al. 2001). When TTC staining was used to quantify and volume of infarcted brain tissue (infarcted brain tissue is white after TTC staining; whereas live brain tissue is dark red/brown) at 48 hours after stroke, brain infarct volume was significantly reduced by Kv2.1, PTEN, Activin Receptor II (ActRII), human PTEN (hPTEN), iNOS, and Kalarin-7 (Kal-7) peptides (FIG. 13), demonstrating therapeutic benefits for the treatment of stroke. As shown in FIG. 13, the C-terminal peptides reduce the size of brain infarcts (white area) with varying degrees of efficacy, with the exception of Kv1.1 or Kv1.3 peptides. When TTC staining was used to quantify the volume of infarcted brain tissue (as described in the methods), at 48 hours after stroke, the mean infarct volume % (±SEM) was significantly reduced by Kv2.1, PTEN, Activin Receptor II (ActRII), human PTEN (hPTEN), iNOS, and Kalarin-7 (Kal-7) C-terminal peptides as shown in the corresponding graph in FIG. 13. Modifying the PTEN peptide by phosphorylation (pPTEN) abolished the neuroprotective effect of the PTEN peptide in the brain, demonstrating that peptide modifications can alter function.

Figure 14:
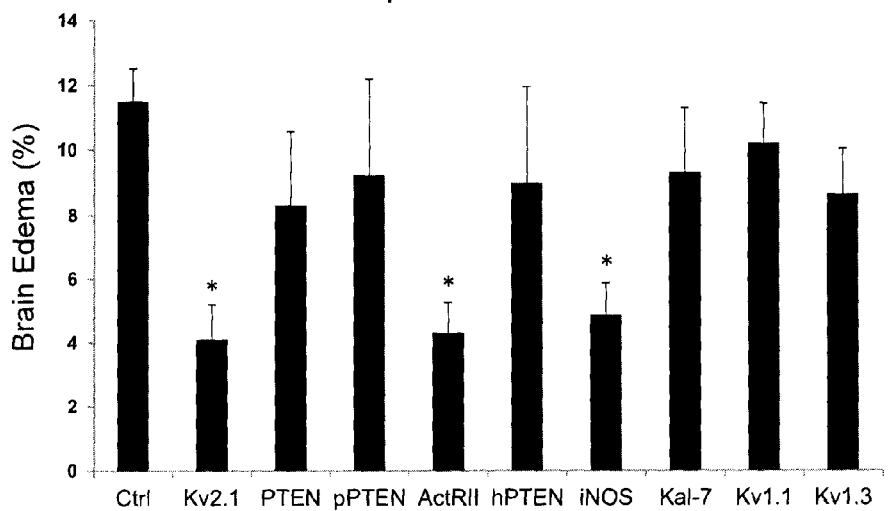
FIG. 14a shows the quantification of functional neurological deficits after middle cerebral artery occlusion (MCAO: stroke) in rats. Animals were scored according to a modified Bederson scale (described in the methods) prior to injury (Baseline), at 8 hours after MCAO, at 24 hours after MCAO, and at 48 hours after MCAO. The normal or baseline score under the modified Bederson system is zero (0) indicative of a lack of neurological deficits, whereas a score of 4 represents severe neurological deficits as described in the methods. Data in the table are presented as the median (25%-75%) interquartile range for the Bederson Score at each time-point. Values that are significantly different from controls (ctrl) at each time-point are highlighted with an asterisk (*=$p<0.05$ relative to control) and shaded in grey.
FIG. 14b shows the quantification of edema (swelling) of the injured brain hemisphere after middle cerebral artery occlusion (MCAO). The data is represented as the percentage increase (Brain Edema %) in the volume of the injured hemisphere after stroke (±SEM), calculated as described in the methods. *=$p<0.05$ relative to control (Ctrl).

Additional functional tests for neurological deficits (Bederson Scoring System) showed that Kv2.1, PTEN, ActRII, human PTEN (hPTEN), iNOS, and Kal-7 peptides significantly reduced neurological deficits after stroke (FIG. 14A). Furthermore, Kv2.1, ActRII, and iNOS peptides significantly reduced brain edema (swelling; a neurotoxic side effect of stroke) at 48 hours after MCAO (FIG. 14B). Edema is a well-known trigger of neuronal dysfunction and degeneration after stroke in humans. Thus, the C-terminal peptides described herein protect against neurodegeneration due to stroke (ischemia) in the central nervous system.

Materials and Methods

Optic Nerve Transection, Retinal Ischemia Induction, and Optic Nerve Crush

Adult female Sprague Dawley rats free of common pathogens were used in all experiments. Animals were kept in a pathogen controlled environment and housed in standard cages equipped with micron air filters. Animals were cared for according to the Canadian Council on animal care.

Optic nerve transection was performed as previously described (Koeberle and Ball 1998; Koeberle and Bahr 2008; Koeberle, Wang et al. 2010; Magharious, D'Onofrio et al. 2011; Magharious, D'Onofrio et al. 2011; Monnier, D'Onofrio et al. 2011). Animals were placed in a stereotaxic frame and anesthetized with Isoflurane (2%; 0.8 L/min oxygen flow rate) delivered through a gas anesthesia mask. Lidocaine eye drops were used to anesthetize the cornea and ophthalmic eye ointment was applied to the cornea to prevent desiccation during surgery. The optic nerve was accessed within the ocular orbit via an incision in the tissue covering the superior border of the orbital bone. The superior orbital contents were dissected and the rectus muscles reflected laterally. In order to allow access to the optic nerve and surrounding dura mater sheath, the eye was rotated laterally by applying traction to the extraocular muscles. The dural sheath surrounding the optic nerve was cut longitudinally, to avoid damaging blood vessels supplying the retina. The optic nerve was gently lifted from the meningeal sheath and transected within 2 mm of the back of the eye. In order to retrogradely label RGCs, gelfoam soaked in 2% Fluorogold (Sigma) was placed over the transected optic nerve stump. The orbital contents were returned to their original location and the initial incision was closed. The optic nerve crush procedure was performed using a similar approach; however, the optic nerve was crushed using fine self-closing forceps for 6 seconds as previously described (Magharious, D'Onofrio et al. 2011; Monnier, D'Onofrio et al. 2011). The orbital contents were then similarly returned to their original location and the initial incision was closed. Following surgery, rats were placed in a recovery cage under a heat lamp and given Ketoprofen to ease post-surgical recovery.

The approach for temporary retinal ischemia (ophthalmic artery ligation) was similar with a few exceptions. this procedure has been previously described (Tatton, Chalmers-Redman et al. 2001). Since the optic nerve was not damaged in this procedure, RGCs had to be retrogradely labeled prior to ischemia. One week prior to surgery, animals received stereotaxic injections of 2% Fluorogold into the CNS target of retinal ganglion cells, the superior colliculus. Injections were performed under gas anesthetic in a stereotaxic apparatus. A Foredom micromotor drill attached to a stereotaxic arm was used to drill holes in the skull above the superior colliculus. Injections were carried out using a 10 µl Hamilton syringe actuated by a computer controlled Picopump (World Precision Instruments). Two injections, each consisting of 2 µl of Fluorogold solution, were delivered at different depths within the superior colliculus at an injection rate of 500 nl/min. The needle was left in place for 10 min after each injection and slowly withdrawn to prevent reflux of the injected solutions up the needle tract. The surgical approach to the optic nerve was identical to that described for optic nerve transection. After a longitudinal cut was made in the meningeal sheath surrounding the optic nerve, the nerve was gently lifted out of the sheath. The meningeal sheath including the ophthalmic artery was then clamped using a calibrated micro-vessel clamp for 45 minutes, after which the clamp was removed to permit vascular reperfusion. The reduction in retinal blood flow and post-surgical reperfusion was verified by fundus examination. Following surgery, rats were placed in a recovery cage under a heat lamp and given Ketoprofen to ease post-surgical recovery.

Intraocular Injections, Optic Nerve Injections, I.V. Injections, I.P. Injections, Eye Drop Application The procedures for intraocular and optic nerve injections have been previously described (Koeberle and Ball 1998; Koeberle and Bahr 2008; Koeberle, Wang et al. 2010; Magharious, D'Onofrio et al. 2011; Magharious, D'Onofrio et al. 2011; Monnier, D'Onofrio et al. 2011). Animals received intraocular injections of each peptide at 3 and 8 days postaxotomy, prior to the onset of RGC apoptosis which occurs at 4-5 days after axotomy. Animals were placed in a stereotaxic frame and anesthetized with isoflurane, delivered through a gas anesthetic mask. The cornea was anesthetized using Alcaine eye drops (Alcon) prior to intraocular injections. A pulled glass micropipette attached to a 10 µl Hamilton syringe via a hydraulic coupling through PEEK tubing was used to deliver 4 µl of a peptide solution (10 mg/ml) into the vitreous chamber of the eye, posterior to the limbus. Care was taken to prevent damage to the lens or anterior structures of the eye. The pipette was held in place for 5 seconds after injection and slowly withdrawn from the eye to prevent reflux. Injections were performed using a surgical microscope in order to visualize pipette entry into the vitreous chamber and confirm delivery of the injected solution.

To directly target RGCs, peptide solutions were injected into the transected optic nerve stump using a 10 microliter Hamilton syringe. A total of 5 microliters of peptide suspension (10 mg/ml) were injected. The majority of the injected fluid will reflux out of the optic nerve during this procedure, so the remaining pool of peptide suspension is left in place when returning the orbital contents to their original positions.

For intravenous injections, a bolus of 1 ml of saline containing 0.5 mg of dissolved peptide was delivered via a tail vein injection at both 24 hours and 8 days following ophthalmic artery ligation (stroke). Injections were delivered using a 25 gauge needle attached to a 5 ml syringe, while animals were anesthetized with isoflurane.

For intraperitoneal injections, 1 ml of saline containing 0.5 mg of dissolved peptide was delivered via a 25 gauge needle attached to a 5 ml syringe, following rapid anesthesia with isoflurane to incapacitate the animal.

For eye drop application of C-terminal peptides, animals were sedated with isoflurane and placed in a stereotaxic frame, in order to reduce the blink reflex. Twenty-five microliters of a peptide suspension (1 mg/ml) was delivered to the surface of the cornea using a micropipetter with a sterile micropipette tip. Eye drops were delivered once per day, on day 1, 2, 3, 4, 5, 6, and day 7 after axotomy.

Quantification of RGC Survival After Injury

Eyes were enucleated, the cornea and lens were removed and the remaining eye cups containing the retinas were fixed in 4% paraformaldehyde at 14 days postaxotomy. Eye cups were fixed for 1 hour and then rinsed in PBS for 15 min. The retinas were then extracted, flat-mounted and cover-slipped using 50:50 glycerol:PBS. Fluorogold staining in RGCs was visualized using an Andor iXon 885+EMCCD camera attached to a Leica DM LFSA microscope. The illumination source was a Sutter Lambda XL with a liquid light guide ensuring even field illumination. RGC densities were sampled at the inner (1/6 retinal eccentricity), mid-periphery (1/2 retinal eccentricity), or outer retina (5/6 retinal eccentricity) of flat-mounted preparations. RGC densities were grouped by retinal eccentricity (inner, middle, outer), and expressed as mean±SEM. ANOVA followed by post hoc analysis using Tukey's post hoc comparisons or Dunnet's post hoc test were used to determine statistical significance between experimental and control samples.

Quantification of RGC Regeneration and GAP-43 Immunohistochemistry

At 21 days after optic nerve crush, animals received intracardial perfusions of 4% paraformaldehyde, and the optic nerves were removed. Nerves were post-fixed in 4% paraformaldehyde overnight at 4° C., and then rinsed in PBS. The fixed nerves were cryoprotected in 30% sucrose in PBS for 7 days and then sectioned using a Leica CM1950 cryostat microtome. Optic nerve sections were incubated overnight at 4° C. in primary antisera directed against growth associated protein-43 (GAP-43) an axon marker in regenerating adult retinal ganglion cells (Meyer, Miotke et al. 1994; Berry, Carlile et al. 1996; Leon, Yin et al. 2000; Su and Cho 2003; Su, Wang et al. 2008; Su, Wang et al. 2009). Primary antisera were diluted in PBS containing 0.3% Triton X-100 and 3% normal serum. Following primary antibody incubation, sections were rinsed 3×15 min. in PBS and incubated with Cy3-labeled secondary antibody for 3 hours at room temperature. Sections were then rinsed 3×15 min. in PBS and cover-slipped with 50:50 glycerol:PBS.

Axon regeneration following optic nerve crush was quantified in longitudinal frozen sections (14 µm thick) of optic nerve, following GAP-43 immunohistochemistry. The number of GAP-43-positive regenerating axon growth cones within bins of the optic nerve, starting at the crush site and proceeding distally, were quantified. The bins were as follows: 0-250 µm, 250-500 µm, and >500 µm. A total of four equally spaced sections through the width of each optic nerve were examined and quantified using a Leica DM LFSA microscope (20× objective) with an Andor iXon 885+ camera, with EM gain applied. The mean number of regenerating axons per section in each bin was then calculated and statistical analysis was performed by ANOVA, and Tukey's post hoc comparisons.

Cortical Neuron Culture

Cortical neuron cultures were made from newborn (P5) rat pups. Cortical samples were triturated 30× using a P1000 pipettor in cold Dubelcco's PBS+glucose. Neurons were plated in 24 well plates coated with poly-d-lysine. 100,000 cells/well were plated in cold Neurobasal A medium+ glutamax+penicillin/streptomycin. Cultures were placed in an incubator (37 celcius, 5% $CO_2$) for 7 days, with half the media changed after 3 days.

After 7 days in culture, the media was replaced with fresh media containing 5 mM glutamate. Experimental samples received various amounts of each peptide, whereas controls received an equivalent volume of PBS (vehicle). After 24 hours, cell survival was quantified using the crystal violet assay: Media was removed from the cells and 200 microliters of 0.2% crystal violet (dissolved in 20% methanol:80% $H_2O$) was added to each well. After 5 minutes, wells were rinsed with distilled water and the plates were dried. Crystal violet was eluted from the cells using 0.1 M sodium citrate in 50% ethanol. 100 microliter samples from each well were then transferred to 96 well plates and absorbance was read at 540 nm. Results were expressed as the relative fold-change in comparison to the control samples that received buffer.

Thromboembolic Model of Middle Cerebral Artery Occlusion (MCAO): Brain Stroke (Ischemia)

In order to examine the effects of the peptide therapeutics described herein, a thromboembolic model of middle cerebral artery occlusion that closely mimics human ischemic brain stroke was used: a clotted segment of blood is injected into the origin of the middle cerebral artery to block blood flow in the corresponding vascular territory of the lateral cerebrum (Wang, Yang et al. 2001).

Formation of Emboli, Revealing the Bifurcation of the Common Carotid Artery and Cerebral Focal Ischemia Model Following deep isoflurane anesthesia via a nose-cone, fur was shaved from the ventral aspect of the neck. The shaved skin was cleaned twice with alternating applications of Proviodine (iodine detergent solution) and 70% ethanol. Following a final application of Proviodine, the surgical field was draped and a midline incision made in the ventral skin and fascia of the neck. Under an operating microscope, the right common carotid artery (CCA), the right external carotid artery (ICA), and the right internal carotid artery (ECA) were carefully isolated and separated from the adjacent vagus nerve. A 6-0 silk suture was loosely tied at the origin of the ECA, and another suture was used to ligate the ECA distally. A sterile modified PE 10 catheter was introduced into the lumen of the right ECA via a small puncture. Ten microliters of blood was withdrawn into the catheter and retained for 15 minutes to allow formation of a clot. The fresh autologous pre-formed clot was used for MCA occlusion. The right CCA and the right ICA were temporarily clamped using microvascular clips. The PE 50 catheter containing a 20 mm long fibrin rich clot was attached to 100 µl Hamilton syringe and introduced into the lumen of the external carotid artery via a small incision. The suture around the origin of the external carotid artery was tightened around the intraluminal catheter to prevent bleeding, and the microvascular clip on the internal carotid artery was removed. The catheter was gently advanced from the ECA into the lumen of the ICA and upwards to the origin of the middle cerebral artery (a total of 17 mm in distance from the bifurcation of the CCA). At this point, the end of the catheter is 1-2 mm away from the origin of the middle cerebral artery. Over 10 seconds, the clot (3.5 µl volume) was gently injected together with 5 µl of sterile saline within the catheter. The catheter was removed 5 minutes after injection, and the right ECA was ligated at its origin. Body temperature was maintained at 37° C. with a heating pad for the duration of surgery, after which the surgical field was closed with 4-0 silk sutures. Subcutaneous injections of Buprenorphine (0.05 mg/kg) were administered to minimize post-surgical discomfort.

Intravenous Injections of Experimental Peptides After MCAO

Experimental animals were anesthetized with isoflurane (via a gas mask attached to a stereotaxic frame) and received tail-vein injections of peptide solutions. Dissolved peptides were injected into the tail-vein at a dose of 1 mg/kg, in a 0.5 ml volume. Control injections consisted of sterile vehicle.

Quantification of Brain Infarct Volume and Edema 48 hours after MCA occlusion isoflurane anesthetized rats were euthanized by decapitation. The brains were removed from the skull and cooled in ice-cold saline for ~5 minutes. For morphometric examination, 2-mm-thick coronal sections were cut using a rat brain matrix. A total of 8 coronal sections were collected, and the sections were stained using a 2% 2,3,5-triphenyltetrazolium chloride solution (TTC). TTC is metabolized by live cells, turning the viable regions of the brain a reddish-brown color; whereas dead regions of brain tissue remain white when viewed with the naked eye. Infarct volumes were calculated from scanned images of the coronal surfaces of brain slices, using the following formula: Infarct volume=(volume of uninjured hemisphere−(volume of injured hemisphere−measured infarct volume))/volume of uninjured hemisphere)×100. This formula serves to quantify the percentage of the injured hemisphere that is infarcted (dead), relative to the uninjured hemisphere volume, in order to account for edema or differences in volumes between the two hemispheres. Brain edema was calculated by comparing the relative volume of the injured brain hemisphere to the uninjured hemisphere using the following formula: Edema %=((volume of injured hemisphere−volume of uninjured hemisphere)/volume of uninjured hemisphere)×100. This calculation yields a percentage value that represents an increase in volume of the injured hemisphere (due to edema) relative to the uninjured hemisphere. Four to six brains for each treatment group or controls were analyzed and the mean±SEM of Infarct Volume % or Brain Edema % was calculated for each group. Statistical significance was determined using Tukey's post hoc tests following an ANOVA at $p<0.05$.

Quantification of Neurological Deficits

Neurological deficits were recorded at 8, 24 and 48 hours after ischemic injury. Neurological deficits were determined using a modified Bederson scoring system. Bederson's scoring system: 0, no observable deficit; 1, forelimb flexion; 2, forelimb flexion plus decreased resistance to lateral push; 3, unidirectional circling; and 4, unidirectional circling plus decreased level of consciousness.

While the present disclosure has been described with reference to what are presently considered to be the examples, it is to be understood that the disclosure is not limited to the disclosed examples. To the contrary, the disclosure is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

TABLE 1

Table of Sequences

| | Amino Acid Sequence | SEQ ID NO: |
|---|---|---|
| C-Terminal Peptide (Target Protein) | | |
| (Natural- Rat) PTEN Phosphatase | DQHSQITKV | 1 |
| (Natural- Human/Rat) Kv2.1 voltage-gated potassium channel | HGSTRDQSI | 2 |
| (Natural- Human/Rat) Kv1.1 voltage-gated potassium channel | NKSKLLTDV | 3 |
| (Natural- Human/Rat) Kv1.3 voltage-gated potassium channel | NIKKIFTDV | 4 |
| (Natural- Human/Rat) Kalirin-7 | PGDPFSTYV | 5 |
| (Natural- Human/Rat) Activin Receptor II (ActRII) | DFPPKESSL | 6 |
| (Natural- Human/Rat) Inducible Nitric Oxide Synthase (iNOS) | LEEPKGTRL | 8 |
| (Natural- Human) PTEN Phosphatase | DQHTQITKV | 9 |
| Protein Transduction Domain | | |
| (Natural- HIV) TAT PTD | YGRKKRRQRRR | 7 |
| (Synthetic) K9 (Lysine 9-mer) | KKKKKKKKK | 10 |
| (Synthetic) R9 (Arginine 9-mer) | RRRRRRRRR | 11 |

REFERENCES

Aras, M. A., R. A. Saadi, et al. (2009). "Zn2+ regulates Kv2.1 voltage-dependent gating and localization following ischemia." *Eur J Neurosci* 30(12): 2250-2257.

Arundine, M. and M. Tymianski (2004). "Molecular mechanisms of glutamate-dependent neurodegeneration in ischemia and traumatic brain injury." *Cell Mol Life Sci* 61(6): 657-668.

Aviles-Trigueros, M., S. Mayor-Torroglosa, et al. (2003). "Transient ischemia of the retina results in massive degeneration of the retinotectal projection: long-term neuroprotection with brimonidine." *Exp Neurol* 184(2): 767-777.

Bahr, M. (2000). "Live or let die—retinal ganglion cell death and survival during development and in the lesioned adult CNS." *Trends Neurosci* 23(10): 483-490.

Barron, K. D., M. P. Dentinger, et al. (1986). "Qualitative and quantitative ultrastructural observations on retinal ganglion cell layer of rat after intraorbital optic nerve crush." *J Neurocytol* 15(3): 345-362.

Berkelaar, M., D. B. Clarke, et al. (1994). "Axotomy results in delayed death and apoptosis of retinal ganglion cells in adult rats." *J Neurosci* 14(7): 4368-4374.

Berry, M., J. Carlile, et al. (1996). "Peripheral nerve explants grafted into the vitreous body of the eye promote the regeneration of retinal ganglion cell axons severed in the optic nerve." *J Neurocytol* 25(2): 147-170.

Bosse, F. (2012). "Extrinsic cellular and molecular mediators of peripheral axonal regeneration." *Cell Tissue Res* 349(1): 5-14.

Cantarella, G., C. Bucolo, et al. (2007). "Protective effects of the sigma agonist Pre-084 in the rat retina." *Br J Ophthalmol* 91(10): 1382-1384.

Chaudhary, P., F. Ahmed, et al. (1999). "Caspase inhibitors block the retinal ganglion cell death following optic nerve transection." *Brain Res Mol Brain Res* 67(1): 36-45.

Colafrancesco, V., V. Parisi, et al. (2011). "Ocular application of nerve growth factor protects degenerating retinal ganglion cells in a rat model of glaucoma." *J Glaucoma* 20(2): 100-108.

Coleman, M. P. and V. H. Perry (2002). "Axon pathology in neurological disease: a neglected therapeutic target." *Trends Neurosci* 25(10): 532-537.

Coleman, M. P. and R. R. Ribchester (2004). "Programmed axon death, synaptic dysfunction and the ubiquitin proteasome system." *Curr Drug Targets CNS Neurol Disord* 3(3): 227-238.

Danylkova, N. O., S. R. Alcala, et al. (2007). "Neuroprotective effects of brimonidine treatment in a rodent model of ischemic optic neuropathy." *Exp Eye Res* 84(2): 293-301.

Dezawa, M. (2002). "Central and peripheral nerve regeneration by transplantation of Schwann cells and transdifferentiated bone marrow stromal cells." *Anat Sci Int* 77(1): 12-25.

Di Polo, A., L. J. Aigner, et al. (1998). "Prolonged delivery of brain-derived neurotrophic factor by adenovirus-infected Muller cells temporarily rescues injured retinal ganglion cells." *Proc Natl Acad Sci USA* 95(7): 3978-3983.

Garcia Valenzuela, E. and S. C. Sharma (1998). "Rescue of retinal ganglion cells from axotomy-induced apoptosis through TRK oncogene transfer." *Neuroreport* 9(14): 3165-3170.

Gaudet, A. D., P. G. Popovich, et al. (2011). "Wallerian degeneration: gaining perspective on inflammatory events after peripheral nerve injury." *J Neuroinflammation* 8: 110.

Goldenberg-Cohen, N., S. Dadon-Bar-El, et al. (2009). "Possible neuroprotective effect of brimonidine in a mouse model of ischaemic optic neuropathy." *Clin Experiment Ophthalmol* 37(7): 718-729.

Hazell, A. S. (2007). "Excitotoxic mechanisms in stroke: an update of concepts and treatment strategies." *Neurochem Int* 50(7-8): 941-953.

Hong, S., C. Y. Kim, et al. (2010). "Ocular hypotensive effects of topically administered agmatine in a chronic ocular hypertensive rat model." *Exp Eye Res* 90(1): 97-103.

Johnston, M. V. (2005). "Excitotoxicity in perinatal brain injury." *Brain Pathol* 15(3): 234-240.

Kanamori, A., M. Naka, et al. (2009). "Tafluprost protects rat retinal ganglion cells from apoptosis in vitro and in vivo." *Graefes Arch Clin Exp Ophthalmol* 247(10): 1353-1360.

Kermer, P., R. Ankerhold, et al. (2000). "Caspase-9: involvement in secondary death of axotomized rat retinal ganglion cells in vivo." *Brain Res Mol Brain Res* 85(1-2): 144-150.

Kermer, P., N. Klocker, et al. (1999). "Long-term effect of inhibition of ced 3-like caspases on the survival of axotomized retinal ganglion cells in vivo." *Exp Neurol* 158(1): 202-205.

Kermer, P., N. Klocker, et al. (1998). "Inhibition of CPP32-like proteases rescues axotomized retinal ganglion cells from secondary cell death in vivo." *J Neurosci* 18(12): 4656-4662.

Kim, H. S., Y. I. Chang, et al. (2007). "Alteration of retinal intrinsic survival signal and effect of alpha2-adrenergic receptor agonist in the retina of the chronic ocular hypertension rat." *Vis Neurosci* 24(2): 127-139.

Klocker, N., F. Braunling, et al. (1997). "In vivo neurotrophic effects of GDNF on axotomized retinal ganglion cells." *Neuroreport* 8(16): 3439-3442.

Koeberle, P. D. and M. Bahr (2004). "Growth and guidance cues for regenerating axons: where have they gone?" *J Neurobiol* 59(1): 162-180.

Koeberle, P. D. and M. Bahr (2008). "The upregulation of GLAST-1 is an indirect antiapoptotic mechanism of GDNF and neurturin in the adult CNS." *Cell Death Differ* 15(3): 471-483.

Koeberle, P. D. and A. K. Ball (1998). "Effects of GDNF on retinal ganglion cell survival following axotomy." *Vision Res* 38(10): 1505-1515.

Koeberle, P. D. and A. K. Ball (1999). "Nitric oxide synthase inhibition delays axonal degeneration and promotes the survival of axotomized retinal ganglion cells." *Exp Neurol* 158(2): 366-381.

Koeberle, P. D. and A. K. Ball (2002). "Neurturin enhances the survival of axotomized retinal ganglion cells in vivo: combined effects with glial cell line-derived neurotrophic factor and brain-derived neurotrophic factor." *Neuroscience* 110(3): 555-567.

Koeberle, P. D., J. Gauldie, et al. (2004). "Effects of adenoviral-mediated gene transfer of interleukin-10, interleukin-4, and transforming growth factor-beta on the survival of axotomized retinal ganglion cells." *Neuroscience* 125(4): 903-920.

Koeberle, P. D. and L. C. Schlichter (2010). "Targeting K(V) channels rescues retinal ganglion cells in vivo directly and by reducing inflammation." *Channels (Austin)* 4(5).

Koeberle, P. D., A. Tura, et al. (2010). "The repulsive guidance molecule, RGMa, promotes retinal ganglion cell survival in vitro and in vivo." *Neuroscience* 169(1): 495-504.

Koeberle, P. D., Y. Wang, et al. (2010). "Kv1.1 and Kv1.3 channels contribute to the degeneration of retinal ganglion cells after optic nerve transection in vivo." *Cell Death Differ* 17(1): 134-144.

Kugler, S., N. Klocker, et al. (1999). "Transduction of axotomized retinal ganglion cells by adenoviral vector administration at the optic nerve stump: an in vivo model system for the inhibition of neuronal apoptotic cell death." *Gene Ther* 6(10): 1759-1767.

Lafuente, M. P., M. P. Villegas-Perez, et al. (2002). "Neuroprotective effects of brimonidine against transient ischemia-induced retinal ganglion cell death: a dose response in vivo study." *Exp Eye Res* 74(2): 181-189.

Lafuente, M. P., M. P. Villegas-Perez, et al. (2002). "Retinal ganglion cell death after acute retinal ischemia is an ongoing process whose severity and duration depends on the duration of the insult." *Neuroscience* 109(1): 157-168.

Lambiase, A., L. Aloe, et al. (2009). "Experimental and clinical evidence of neuroprotection by nerve growth factor eye drops: Implications for glaucoma." *Proc Natl Acad Sci USA*.

Leon, S., Y. Yin, et al. (2000). "Lens injury stimulates axon regeneration in the mature rat optic nerve." *J Neurosci* 20(12): 4615-4626.

Lingor, P., P. Koeberle, et al. (2005). "Down-regulation of apoptosis mediators by RNAi inhibits axotomy-induced retinal ganglion cell death in vivo." *Brain* 128(Pt 3): 550-558.

Lingor, P., L. Tonges, et al. (2008). "ROCK inhibition and CNTF interact on intrinsic signalling pathways and differentially regulate survival and regeneration in retinal ganglion cells." *Brain* 131(Pt 1): 250-263.

Magharious, M., P. M. D'Onofrio, et al. (2011). "Quantitative iTRAQ Analysis of Retinal Ganglion Cell Degeneration after Optic Nerve Crush." *J Proteome Res*.

Magharious, M. M., P. M. D'Onofrio, et al. (2011). "Methods for experimental manipulations after optic nerve transection in the Mammalian CNS." *J Vis Exp*(51).

Magharious, M. M., P. M. D'Onofrio, et al. (2011). "Optic nerve transection: a model of adult neuron apoptosis in the central nervous system." *J Vis Exp*(51).

Marrazzo, A., F. Caraci, et al. (2005). "Neuroprotective effects of sigma-1 receptor agonists against beta-amyloid-induced toxicity." *Neuroreport* 16(11): 1223-1226.

Metoki, T., H. Ohguro, et al. (2005). "Study of effects of antiglaucoma eye drops on N-methyl-D-aspartate-induced retinal damage." *Jpn J Ophthalmol* 49(6): 453-461.

Mey, J. and S. Thanos (1993). "Intravitreal injections of neurotrophic factors support the survival of axotomized retinal ganglion cells in adult rats in vivo." *Brain Res* 602(2): 304-317.

Meyer, R. L., J. A. Miotke, et al. (1994). "Injury induced expression of growth-associated protein-43 in adult mouse retinal ganglion cells in vitro." *Neuroscience* 63(2): 591-602.

Misantone, L. J., M. Gershenbaum, et al. (1984). "Viability of retinal ganglion cells after optic nerve crush in adult rats." *J Neurocytol* 13(3): 449-465.

Monnier, P. P., P. M. D'Onofrio, et al. (2011). "Involvement of caspase-6 and caspase-8 in neuronal apoptosis and the regenerative failure of injured retinal ganglion cells." *J Neurosci* 31(29): 10494-10505.

Nakabayashi, M. (2004). "Review of the ischemia hypothesis for ocular hypertension other than congenital glaucoma and closed-angle glaucoma." *Ophthalmoloqica* 218(5): 344-349.

Nakazawa, T., M. Tamai, et al. (2002). "Brain-derived neurotrophic factor prevents axotomized retinal ganglion cell death through MAPK and PI3K signaling pathways." *Invest Ophthalmol Vis Sci* 43(10): 3319-3326.

Osborne, N. N., J. Melena, et al. (2001). "A hypothesis to explain ganglion cell death caused by vascular insults at the optic nerve head: possible implication for the treatment of glaucoma." *Br J Ophthalmol* 85(10): 1252-1259.

Pal, S., K. A. Hartnett, et al. (2003). "Mediation of neuronal apoptosis by Kv2.1-encoded potassium channels." *J Neurosci* 23(12): 4798-4802.

Pal, S. K., K. Takimoto, et al. (2006). "Apoptotic surface delivery of K+ channels." *Cell Death Differ* 13(4): 661-667.

Peinado-Ramon, P., M. Salvador, et al. (1996). "Effects of axotomy and intraocular administration of NT-4, NT-3, and brain-derived neurotrophic factor on the survival of adult rat retinal ganglion cells. A quantitative in vivo study." *Invest Ophthalmol Vis Sci* 37(4): 489-500.

Quigley, H. A., R. W. Nickells, et al. (1995). "Retinal ganglion cell death in experimental glaucoma and after axotomy occurs by apoptosis." *Invest Ophthalmol Vis Sci* 36(5): 774-786.

Redman, P. T., K. He, et al. (2007). "Apoptotic surge of potassium currents is mediated by p38 phosphorylation of Kv2.1." *Proc Natl Acad Sci USA* 104(9): 3568-3573.

Sautter, J. and B. A. Sabel (1993). "Recovery of brightness discrimination in adult rats despite progressive loss of retrogradely labelled retinal ganglion cells after controlled optic nerve crush." *Eur J Neurosci* 5(6): 680-690.

Schmidt, K. G., L. E. Pillunat, et al. (2004). "[Ischemia and hypoxia. An attempt to explain the different rates of retinal ganglion cell death in glaucoma]." *Ophthalmologe* 101 (11): 1071-1075.

Seki, M. and S. A. Lipton (2008). "Targeting excitotoxic/free radical signaling pathways for therapeutic intervention in glaucoma." *Prog Brain Res* 173: 495-510.

Seki, M., T. Tanaka, et al. (2005). "Topically administered timolol and dorzolamide reduce intraocular pressure and protect retinal ganglion cells in a rat experimental glaucoma model." *Br J Ophthalmol* 89(4): 504-507.

Sievers, J., B. Hausmann, et al. (1987). "Fibroblast growth factors promote the survival of adult rat retinal ganglion cells after transection of the optic nerve." *Neurosci Lett* 76(2): 157-162.

Stevenson, J. A. (1987). "Growth of retinal ganglion cell axons following optic nerve crush in adult hamsters." *Exp Neurol* 97(1): 77-89.

Su, H. X. and E. Y. Cho (2003). "Sprouting of axon-like processes from axotomized retinal ganglion cells induced by normal and preinjured intravitreal optic nerve grafts." *Brain Res* 991(1-2): 150-162.

Su, Y., F. Wang, et al. (2009). "Axonal regeneration of optic nerve after crush in Nogo66 receptor knockout mice." *Neurosci Lett* 460(3): 223-226.

Su, Y., F. Wang, et al. (2008). "Axonal regeneration after optic nerve crush in Nogo-A/B/C knockout mice." *Mol Vis* 14: 268-273.

Tatton, W. G., R. M. Chalmers-Redman, et al. (2001). "Apoptosis and anti-apoptosis signalling in glaucomatous retinopathy." *Eur J Ophthalmol* 11 Suppl 2: S12-22.

Toda, N. and M. Nakanishi-Toda (2007). "Nitric oxide: ocular blood flow, glaucoma, and diabetic retinopathy." *Prog Retin Eye Res* 26(3): 205-238.

Vargas, M. E. and B. A. Barres (2007). "Why is Wallerian degeneration in the CNS so slow?" *Annu Rev Neurosci* 30: 153-179.

Villegas-Perez, M. P., M. Vidal-Sanz, et al. (1988). "Influences of peripheral nerve grafts on the survival and regrowth of axotomized retinal ganglion cells in adult rats." *J Neurosci* 8(1): 265-280.

Villegas-Perez, M. P., M. Vidal-Sanz, et al. (1993). "Rapid and protracted phases of retinal ganglion cell loss follow axotomy in the optic nerve of adult rats." *J Neurobiol* 24(1): 23-36.

Wang, C. X., T. Yang, et al. (2001). "An improved version of embolic model of brain ischemic injury in the rat." *J Neurosci Methods* 109(2): 147-151.

Wu, W. C., C. C. Lai, et al. (2004). "GDNF gene therapy attenuates retinal ischemic injuries in rats." *Mol Vis* 10: 93-102.

Yip, H. K. and K. F. So (2000). "Axonal regeneration of retinal ganglion cells: effect of trophic factors." *Prog Retin Eye Res* 19(5): 559-575.

---

The invention claimed is:

1. A method for inhibiting neuronal cell death in an animal or cell in need thereof comprising administering at least one C-terminal peptide, wherein the C-terminal peptide comprises the amino acid sequence as shown in SEQ ID NOs: 1-6, 8 or 9 or a conservatively substituted functional variant thereof; wherein the C-terminal peptide is 9 to 12 amino acids in length.

2. The method of claim 1, comprising administering at least two of the C-terminal peptides.

3. The method of claim 2, wherein the at least two C-terminal peptides comprise SEQ ID NO:1 and SEQ ID NO: 2 or conservatively substituted functional variants thereof; or SEQ ID NO:9 and SEQ ID NO: 2 or conservatively substituted functional variants thereof.

4. The method of claim 1, wherein a protein transduction domain is conjugated to the at least one C-terminal peptide.

5. The method of claim 1, wherein the neuronal cell is a retinal ganglion cell.

6. The method of claim 1, wherein the animal has a retinal degenerative disorder; or had or is having a central nervous system (CNS) insult; or a peripheral nervous system (PNS) insult.

7. The method of claim 6, wherein the retinal degenerative disorder is glaucoma, age related macular degeneration, diabetic retinopathy, uveoretinitis, vitreoretinopathy, photoreceptor cell dystrophy or degeneration, retinitis pigmentosa, retinal ischemia, retinal detachment, optic neuropathy or optic atrophy.

8. The method of claim 1, wherein the C-terminal peptide comprises the amino acid sequence as shown in SEQ ID NOs:1, 2, 5, 6, 8 or 9 or a conservatively substituted functional variant thereof and the animal had or is having a stroke.

9. The method of claim 6, wherein the CNS insult is to the brain or spinal cord and is traumatic CNS injury, stroke, concussion, neurodegenerative diseases, or brain damage caused by tumors or surgical procedures.

10. The method of claim 1, wherein the animal is human.

11. The method of claim 1, wherein the at least one C-terminal peptide is administered intravenously, intraocularly, via optic nerve injection, topically, by surgical implantation or intraperitoneally.

12. The method of claim 1, wherein the at least one C-terminal peptide comprises the amino acid sequence as shown in SEQ ID NOs:1, 2, 3, 5, 6, 8 or 9 or a conservatively substituted functional variant thereof and the at least one C-terminal peptide is administered topically in the eye.

* * * * *

SEQUENCE LISTING

```
<160> NUMBER OF SEQ ID NOS: 11

<210> SEQ ID NO 1
<211> LENGTH: 9
<212> TYPE: PRT
<213> ORGANISM: Rattus rattus

<400> SEQUENCE: 1

Asp Gln His Ser Gln Ile Thr Lys Val
1               5

<210> SEQ ID NO 2
<211> LENGTH: 9
<212> TYPE: PRT
<213> ORGANISM: Homo sapiens

<400> SEQUENCE: 2

His Gly Ser Thr Arg Asp Gln Ser Ile
1               5

<210> SEQ ID NO 3
<211> LENGTH: 9
<212> TYPE: PRT
<213> ORGANISM: Homo sapiens

<400> SEQUENCE: 3

Asn Lys Ser Lys Leu Leu Thr Asp Val
1               5

<210> SEQ ID NO 4
<211> LENGTH: 9
<212> TYPE: PRT
<213> ORGANISM: Homo sapiens

<400> SEQUENCE: 4

Asn Ile Lys Lys Ile Phe Thr Asp Val
```

```
<210> SEQ ID NO 5
<211> LENGTH: 9
<212> TYPE: PRT
<213> ORGANISM: Homo sapiens

<400> SEQUENCE: 5

Pro Gly Asp Pro Phe Ser Thr Tyr Val
1               5

<210> SEQ ID NO 6
<211> LENGTH: 9
<212> TYPE: PRT
<213> ORGANISM: Homo sapiens

<400> SEQUENCE: 6

Asp Phe Pro Pro Lys Glu Ser Ser Leu
1               5

<210> SEQ ID NO 7
<211> LENGTH: 11
<212> TYPE: PRT
<213> ORGANISM: Human immunodeficiency virus

<400> SEQUENCE: 7

Tyr Gly Arg Lys Lys Arg Arg Gln Arg Arg Arg
1               5                   10

<210> SEQ ID NO 8
<211> LENGTH: 9
<212> TYPE: PRT
<213> ORGANISM: Homo sapiens

<400> SEQUENCE: 8

Leu Glu Glu Pro Lys Gly Thr Arg Leu
1               5

<210> SEQ ID NO 9
<211> LENGTH: 9
<212> TYPE: PRT
<213> ORGANISM: Homo sapiens

<400> SEQUENCE: 9

Asp Gln His Thr Gln Ile Thr Lys Val
1               5

<210> SEQ ID NO 10
<211> LENGTH: 9
<212> TYPE: PRT
<213> ORGANISM: Artificial Sequence
<220> FEATURE:
<223> OTHER INFORMATION: Synthetic construct

<400> SEQUENCE: 10

Lys Lys Lys Lys Lys Lys Lys Lys Lys
1               5

<210> SEQ ID NO 11
```

```
<211> LENGTH: 9
<212> TYPE: PRT
<213> ORGANISM: Artificial Sequence
<220> FEATURE:
<223> OTHER INFORMATION: Synthetic construct

<400> SEQUENCE: 11

Arg Arg Arg Arg Arg Arg Arg Arg Arg
1               5
```